US008292931B2

(12) United States Patent
Forrest

(10) Patent No.: US 8,292,931 B2
(45) Date of Patent: Oct. 23, 2012

(54) METHOD AND DEVICE FOR PLACING MATERIALS IN THE SPINE

(76) Inventor: Leonard Edward Forrest, Mount Pleasant, SC (US)

(*) Notice: Subject to any disclaimer, the term of this patent is extended or adjusted under 35 U.S.C. 154(b) by 49 days.

(21) Appl. No.: 13/006,699

(22) Filed: Jan. 14, 2011

(65) Prior Publication Data

US 2011/0166603 A1    Jul. 7, 2011

Related U.S. Application Data

(63) Continuation-in-part of application No. 12/949,997, filed on Nov. 19, 2010, which is a continuation of application No. 11/972,815, filed on Jan. 11, 2008, now Pat. No. 7,905,863, which is a continuation-in-part of application No. 11/112,475, filed on Apr. 23, 2005, now Pat. No. 7,322,962.

(60) Provisional application No. 60/564,838, filed on Apr. 23, 2004, provisional application No. 60/572,930, filed on May 20, 2004, provisional application No. 60/586,627, filed on Jul. 9, 2004, provisional application No. 60/588,582, filed on Jul. 16, 2004, provisional application No. 60/588,587, filed on Jul. 16, 2004.

(51) Int. Cl.
*A61B 17/88* (2006.01)

(52) U.S. Cl. ........................................ 606/279

(58) Field of Classification Search ............... 623/17.11; 606/246, 279, 79, 84, 85, 92–94, 86 A
See application file for complete search history.

(56) References Cited

U.S. PATENT DOCUMENTS 5,221,253 A    6/1993   Coll
5,292,330 A    3/1994   Shutt
5,980,504 A    11/1999  Sharkey et al.
6,007,570 A    12/1999  Sharkey et al.
6,073,051 A    6/2000   Sharkey et al.
6,095,149 A    8/2000   Sharkey et al.
6,122,549 A    9/2000   Sharkey et al.
6,245,054 B1   6/2001   Fuimaono et al.
6,258,086 B1   7/2001   Ashley et al.
6,261,311 B1   7/2001   Sharkey et al.
6,283,960 B1   9/2001   Ashley
6,409,727 B1   6/2002   Bales et al.
6,517,568 B1   2/2003   Sharkey et al.
6,547,810 B1   4/2003   Sharkey et al.
6,562,033 B2   5/2003   Shah et al.

(Continued)

FOREIGN PATENT DOCUMENTS

WO    9742996 A1    11/1997

(Continued)

*Primary Examiner* — Eduardo C Robert
*Assistant Examiner* — David Comstock
(74) *Attorney, Agent, or Firm* — B. Craig Killough

(57) ABSTRACT

A device and method for removing tissue, and if required, other undesired materials from an intervertebral disc or vertebral body. An elongated arcuate, and preferably S-shaped tool is used to progressively remove material from the interior of the mammalian intervertebral disc or vertebral body. A sheath introduces the elongated tool by a posterior, posterolateral or lateral approach. The shape of the elongated tool is formed within a guide or lumen of the sheath for transportation through the sheath. The elongated tool assumes its predetermined arcuate shape when no pressure or force is applied to the tool by the sheath as the elongated tool exits the sheath. The device and method allow positioning of new material in the intervertebral disc and/or vertebral body. The new material may be tissue, therapeutic agents, mechanical devices such as spacers, or agents that will fuse vertebral bodies.

23 Claims, 29 Drawing Sheets

U.S. PATENT DOCUMENTS

| | | |
|---|---|---|
| 6,595,959 B1 | 7/2003 | Stratienko |
| 6,602,248 B1 | 8/2003 | Sharps |
| 6,604,003 B2 | 8/2003 | Fredricks et al. |
| 6,638,276 B2 | 10/2003 | Sharkey et al. |
| 6,726,685 B2 | 4/2004 | To et al. |
| 6,733,496 B2 | 5/2004 | Sharkey et al. |
| 6,821,276 B2 | 11/2004 | Lambrecht et al. |
| 6,832,997 B2 | 12/2004 | Uchida et al. |
| 2001/0031963 A1 | 10/2001 | Sharkey et al. |
| 2002/0022830 A1 | 2/2002 | Sharkey et al. |
| 2002/0082585 A1 | 6/2002 | Carroll |
| 2003/0130712 A1 | 7/2003 | Smits |
| 2003/0181964 A1 | 9/2003 | Sharkey et al. |
| 2003/0199960 A1 | 10/2003 | Paskar |
| 2003/0225331 A1 | 12/2003 | Diederich et al. |
| 2004/0015215 A1 | 1/2004 | Fredricks et al. |
| 2004/0015218 A1 | 1/2004 | Finch et al. |
| 2004/0083002 A1 | 4/2004 | Belef et al. |
| 2004/0087994 A1 | 5/2004 | Suddaby |
| 2004/0102824 A1 | 5/2004 | Sharkey et al. |
| 2004/0111136 A1 | 6/2004 | Sharkey et al. |
| 2004/0111137 A1 | 6/2004 | Sharkey et al. |
| 2004/0127963 A1 | 7/2004 | Uchida et al. |
| 2004/0193045 A1 | 9/2004 | Scarborough et al. |

FOREIGN PATENT DOCUMENTS

| | | |
|---|---|---|
| WO | 0105330 A1 | 1/2001 |

METHOD AND DEVICE FOR PLACING MATERIALS IN THE SPINE

Applicant claims the benefit of each of the following priority documents: U.S. application Ser. No. 12/949,997 filed Nov. 19, 2010, which claimed the benefit of U.S. application Ser. No. 11/972,815 filed Jan. 11, 2008, which claimed the benefit of U.S. application Ser. No. 11/112,475 filed Apr. 23, 2005, now issued U.S. Pat. No. 7,322,962 issued Jan. 29, 2008, which claimed the benefit of U.S. Provisional Application Ser. No. 60/564,838 filed Apr. 23, 2004, and which claimed the benefit of U.S. Provisional Application Ser. No. 60/572,930 filed May 20, 2004, and which claimed the benefit of U.S. Provisional Application Ser. No. 60/586,627 filed Jul. 9, 2004 and which claimed the benefit of U.S. Provisional Application Ser. No. 60/588,582 filed Jul. 16, 2004, and which claimed the benefit of U.S. Provisional Application Ser. No. 60/588,587 filed Jul. 16, 2004.

FIELD OF INVENTION

This invention and method relate to the treatment of spine or evacuation of components of the spine.

BACKGROUND OF THE INVENTION

The intervertebral disc is comprised of an outer annulus fibrosis and an internal nucleus pulposus. The healthy annulus is comprised of 10-20 lamellae forming a concentric ring of collagen and elastic fibers around the nucleus while the healthy nucleus pulposus is ovoid and composed of a gelatinous mucoprotein within the confines of the annulus fibrosis.

In the healthy normal disc, the annulus is thick and the internal wall is strong and without significant defects. Aging and trauma cause multiple and varied defects of the annulus as well as changes in the nucleus. These defects are a source of pain for many individuals. It is widely accepted that the defects which actually do cause pain are either posterior or postero-lateral. By far, it is most common that symptomatic defects are posterior and/or unilateral postero-lateral. Symptomatic defects which are posterior and bilateral postero-lateral certainly do exist but are definitely less common. On the other hand, degenerative changes with defects along the inner annular wall can be found commonly in various other segments of the inner annular wall (anteriorially, antero-laterally on either or both sides, and laterally on either or both sides. These defects are understood to be asymptomatic, but nevertheless are common.

Radiofrequency is used to treat internal intervertebral disc disruption. Forward pressure is applied to circumvent the nucleus adjacent to the inner annular wall, leverage with the forward pressure against the annular wall opposite to the portion attempting to be treated, or drive through the annular tissue which is intended to be treated.

The catheter is advanced around the inside of the nucleus pulposus adjacent to the inner annular wall. However, in the spectrum of discs requiring treatment, ideal discs are infrequently encountered. The result is that the tip of the catheter, even with a bent and/or capped tip gets caught in defects in the wall, making the advancement difficult or impossible. This frequently results in kinking of the catheter (which then typically must be removed), lodging into the defect (presumably worsening the defect), going through the annular wall (obviously creating a through and through defect in the annular wall and even potentially puncturing or damaging nerve or vascular structures), and ultimately making the intended treatment sub-optimal or even impossible. Additionally, in such situations there has been further damage caused to the disc by the catheter. The defects into which the catheter can inadvertently probe can be the defect, or defects, intended to be treated. Alternately, a defect in the anterior, antero-lateral, or lateral wall can equally be entered inadvertently and cause a disruption of the procedure. Degenerative disc walls commonly contain multiple such defects, as well as thinning of the wall, which are all too frequently penetrated.

The insertion of material into the disc or vertebral body can strengthen a diseased or damaged disc or vertebral body. Such materials may be man-made, or the materials may be biological materials. Regenerative materials show great promise in regenerating damaged and diseased tissue. Proper positioning of these materials within a disc or a vertebral body may be important in achieving desired results.

SUMMARY OF THE INVENTION

The invention is a device and method for removing tissue, and if required, other undesired materials from an intervertebral disc or vertebral body. An elongated arcuate, and preferably S-shaped tool is used to progressively remove material from the interior of the mammalian intervertebral disc or vertebral body. A sheath introduces the elongated tool by a posterior, postero-lateral or lateral approach. The shape of the elongated tool is formed within a guide or lumen of the sheath for transportation through the sheath. The elongated tool assumes its predetermined arcuate shape when no pressure or force is applied to the tool by the sheath as the elongated tool exits the sheath.

The device and method allow positioning of new material in the intervertebral disc and/or vertebral body. The new material may be tissue, therapeutic agents, mechanical devices such as spacers, or agents that will fuse vertebral bodies.

DESCRIPTION OF PREFERRED EMBODIMENTS

Figure 1:
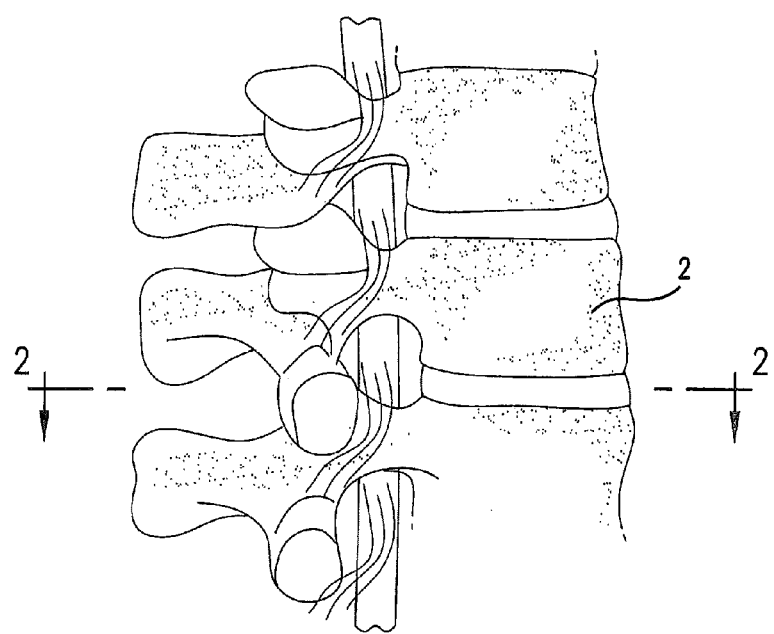
FIG. 1 shows a partial lateral view of a portion of a human spine.
Figure 2:
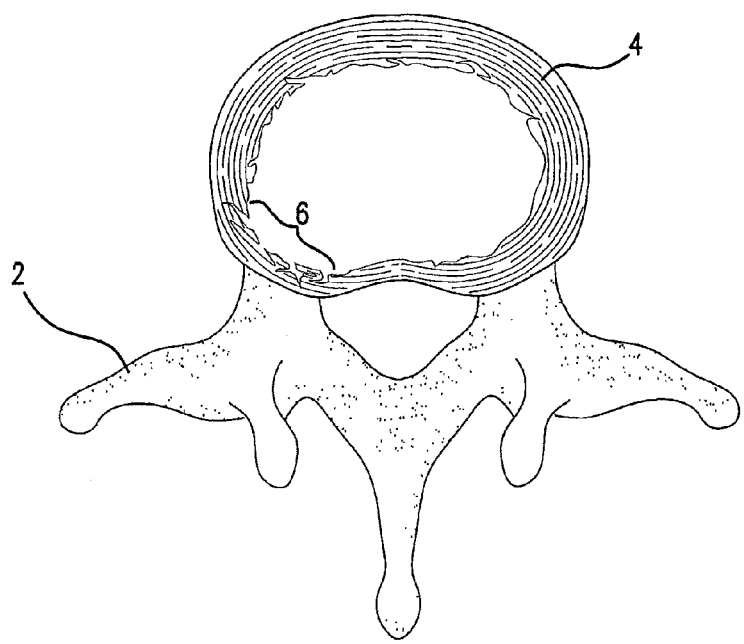
FIG. 2 is a sectioned view taken essentially along line 2-2 of FIG. 1.

Turning now to the drawing figures, FIG. 1 shows a partial view of a mammalian spine, and more particularly, a human spine 2. FIG. 2 is a sectioned view taken essentially along line 2-2 of FIG. 1, and shows an annular wall of a disc 4 of a human spine. The inner annular wall is rough, or jagged, due to trauma, aging and/or disease. Treatment of the portion of the disc labeled 6 is indicated due to its condition. Advancement of a catheter into the disc, and around the wall of the disc to the area to be treated is difficult, since the tip of the catheter is likely to engage the rough, jagged inner annular wall. The catheter is preferred to be laid against the portion of the disc intended to be treated, minimizing the course of the catheter within the disc, yet assuring good contact of the catheter with the portion of the disc to be treated. The angle of entry into the disc should be maximized to accommodate a spectrum of operative conditions and introducer/needle placements. The portion of the disc requiring treatment as contemplated in this embodiment is postero-lateral (one side or both), plus or minus a portion of the posterior wall. The route to the interior of the disc must be straight. For humans, the distance from the outer layer of skin to interior of the disc is approximately 12 to 30 centimeters, depending upon the size of the individual upon which the process is performed.

Figure 4:
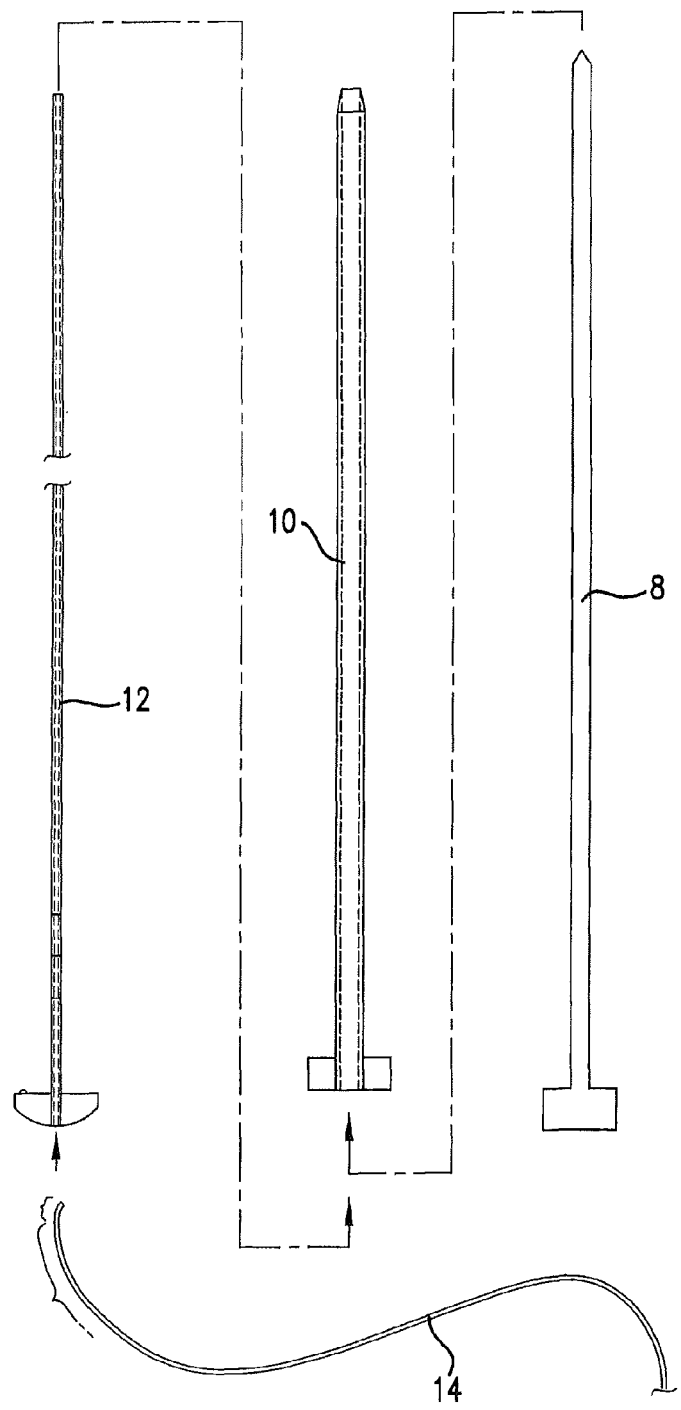
FIG. 4 is an exploded view showing the introducer, non-conductive sheath, stylet and catheter.

FIG. 4 shows the primary elements of the apparatus of the present invention. A stylet 8 is inserted into an introducer 10. A lumen in the form of a sheath 12 is subsequently inserted into the introducer, and a catheter 14 having a preformed S shape is advanced through the sheath. The lumen acts as a guide through which the S-shaped tool such, catheter, is transported. The guide may take other forms that will assist transportation of the tool into the disc, such as a track or a wire that the tool engages. In one embodiment, the guide is part of the introducer, such as a lumen formed therein. The introducer is preferred to be straight for ease of placement and due to the distance from the skin to the interior of the disc. The introducer will generally have a length in excess of 10 centimeters.

The stylet and introducer, which may be needle like, form a passage into the disc through the posterior wall of the disc on the side opposite that requiring treatment. The stylet is intended to keep the tissue from accumulating within the advancing introducer.

The introducer is advanced under fluoroscopic guidance lateral to the superior articular process. The annulus is punctured and the introducer may be advanced initially approximately one-third to one-half of the distance of the disc, as can be judged by operators skilled in performing such procedures.

Figure 5:
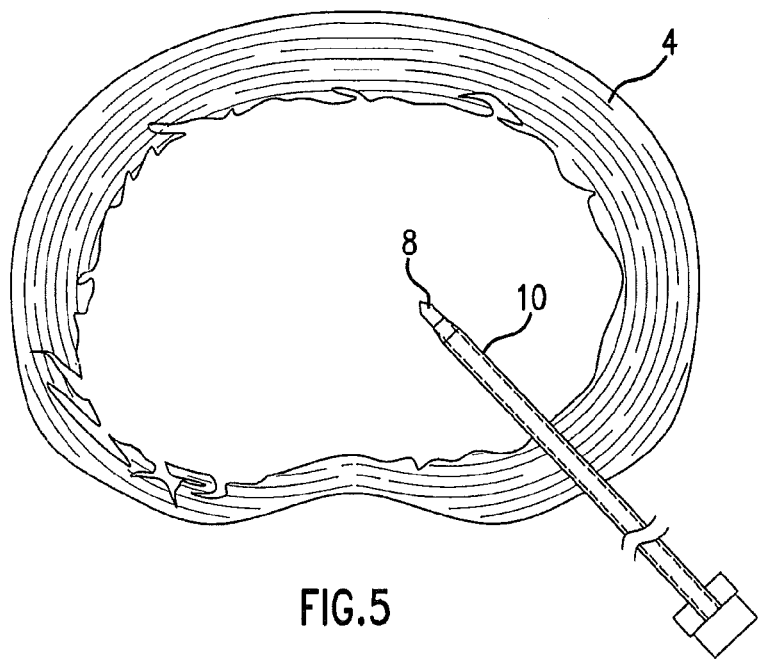
FIG. 5 shows the introducer with stylet in place and having penetrated the annular wall of the disc.
Figure 6:
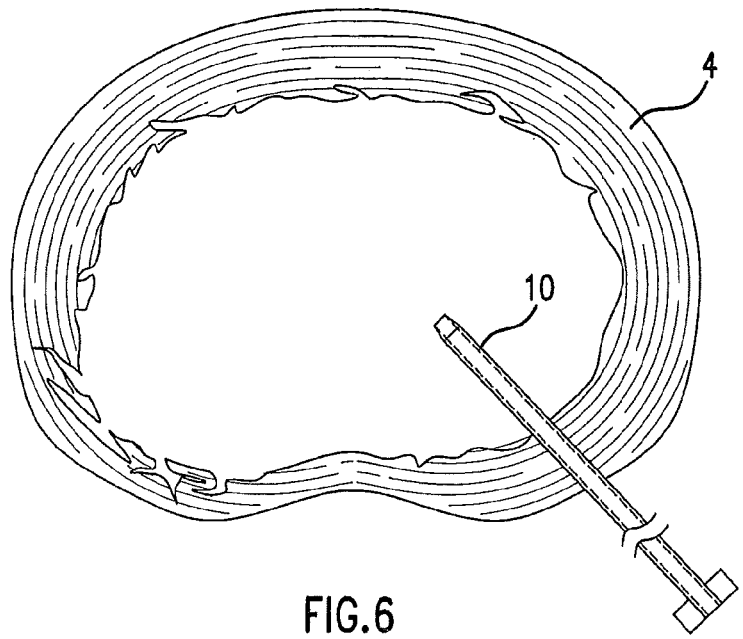
FIG. 6 shows the introducer with the stylet removed.

FIG. 5 shows the introducer with stylet in position. The sharp point of the stylet is driven through the wall of the disc, along with the introducer. The stylet is then removed. FIG. 6.

After the stylet and introducer pierce the annular wall of the disc and access the interior of the disc, the stylet is removed and is replaced with a lumen, which may be a sheath. A pre-formed, S-shaped catheter or other tool having memory retention properties is contained within the straight sheath. The straight sheath is inserted through the introducer for introduction into the disc. The catheter is straightened by the pressure from the walls of the sheath, but the catheter regains its S-shape as it exits the sheath.

The sheath locks into place at the external end of the introducer. When locked into place, the catheter sheath will protrude from the tip of the introducer. The sheath remains well contained within the disc nucleus and not in the proximity of the opposing annular wall but may be advanced or retracted as necessary for catheter positioning.

The sheath is preferred to be made of nonconductive material having thermal insulative properties sufficient to avoid undesired heating of tissues and structures outside of the disc, even if the heating portion of the catheter comes into close proximity or even contact with this sheath. The sheath may be straight, or slightly curved, and capable of advancing through the introducer once the stylet is removed. It has sufficient rigidity to maintain a portion of the catheter in a straight position while that portion of the catheter is in the sheath. The sheath is capable of externally locking at an upper portion into the introducer at the hub.

The non-conductive catheter sheath ensures that no inadvertent heating of the introducer occurs. Heating may cause significant unwanted damage to skin, subcutaneous tissue, fat, muscle, and even nerve.

Figure 7:
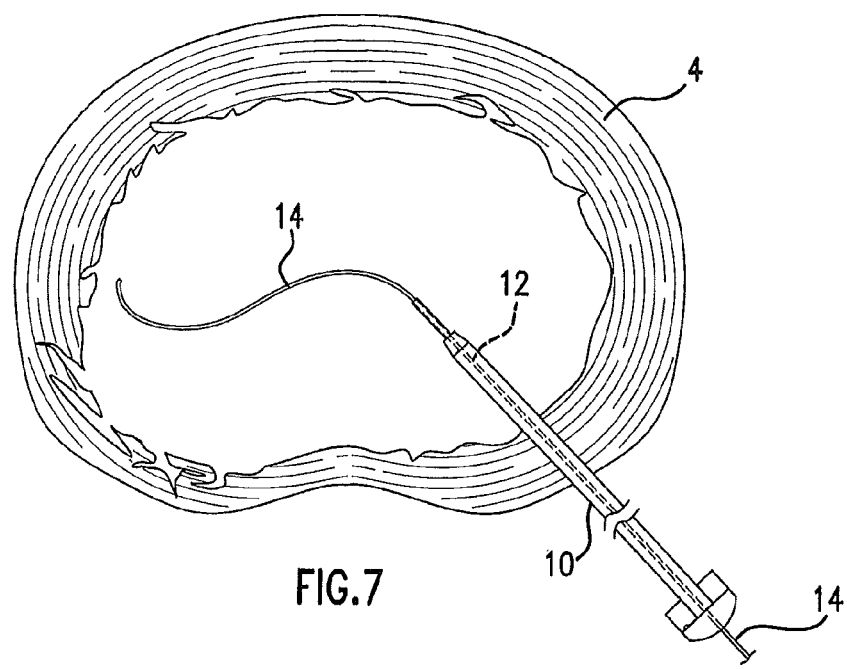
FIG. 7 shows the non-conductive sheath inserted into and through the introducer, with the S-shaped catheter advanced through the sheath.
Figure 8:
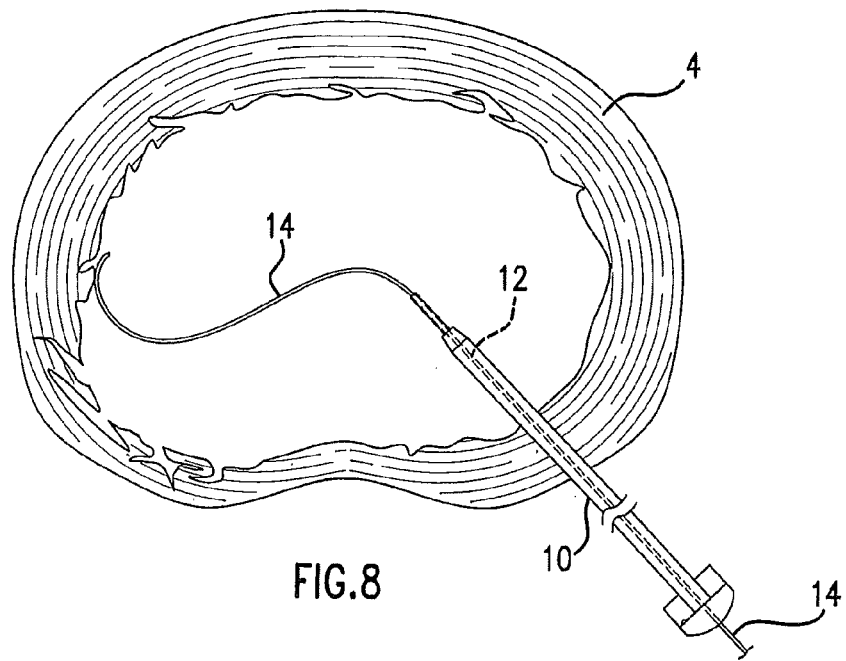
FIG. 8 shows the S-shaped catheter extended as required through the sheath.

The sheath is inserted into the lumen of the introducer, while the introducer remains in position within the disc as shown in FIG. 6. In FIG. 7, the catheter is advanced through the sheath. As the S-shaped catheter exits the sheath within the interior of the disc, the catheter, due to memory retention properties, and with no pressure applied, assumes its S-shape, as shown in FIG. 7. In FIG. 8, the catheter continues to advance and contacts the lateral inner annular wall of the side on which the postero-lateral wall is to be treated. Catheter advancement may be fluoroscopically monitored.

Figure 9:
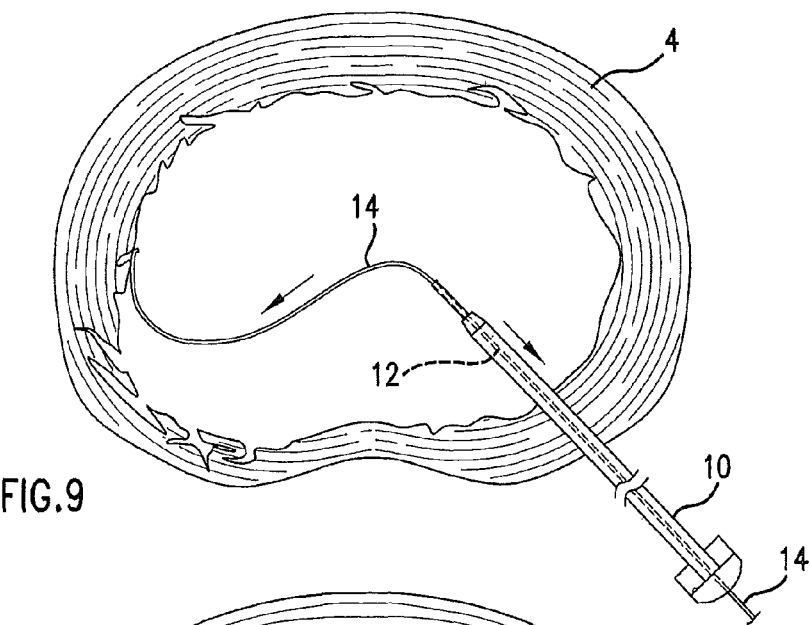
FIG. 9 demonstrates the introducer and sheath being retracted to position the catheter.

FIG. 9 demonstrates the introducer being retracted from the disc as the catheter is advanced. This combination of movements causes the catheter to move toward the postero-lateral and posterior wall which is the intended side of treatment. As shown, the introducer and sheath are retracted until the catheter is in position against the site to be treated. Positioning of the sheath and the catheter may be monitored fluoroscopically.

Figure 10:
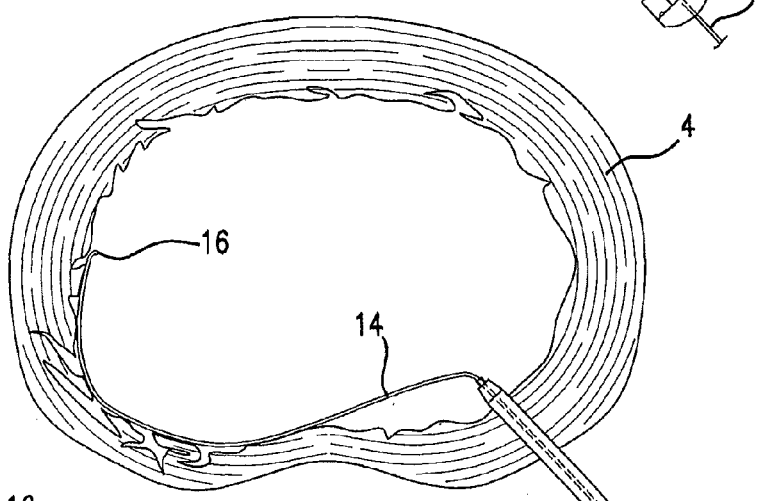
FIG. 10 shows the introducer and sheath retracted, and the catheter positioned against the inner annular wall defect.
Figure 11:
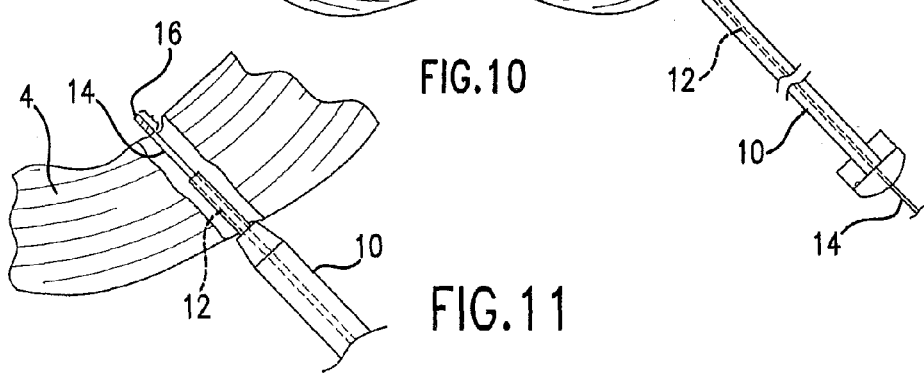
FIG. 11 demonstrates the device being withdrawn from the disc and the iatrogenecally created defect being sealed.

As shown in FIG. 10, the introducer is retracted until the catheter rests against the lateral posterior wall to be treated. The lateral posterior wall to be treated is opposite the side of the posterior wall that the introducer has penetrated. Heat or radio frequency can be applied to the disc wall by means of the catheter. Other therapeutic procedures may be applied by use of an appropriate catheter. The catheter may then be retracted, and the introducer is retracted from the disc as shown in FIG. 11. Either the tip of this catheter can be differentially heated to seal the entry defect, or the S shaped catheter is removed and replaced with a straight catheter with a heating element at the tip. Heating of the tip as the introducer and elongated tool, such as the catheter, are withdrawn seals the entry defect. Alternately, a catheter with a portal at the tip to inject a sealant of this entry defect may be used.

For positions between the extremes of acute and obtuse, the length of sheath or elongated tool versus disbursed catheter will determine the position at which the catheter tip will come into contact with the opposite lateral wall. Recognition of the goal of having the catheter contact the mid portion of the lateral wall of the side to be treated, and monitoring progress under fluoroscopy will facilitate ideal catheter placement.

In this embodiment, the portion of the elongated tool, such as a catheter, has an S shape when no material pressure or force is applied to the catheter. The catheter may be formed of nitinol, which is sufficiently flexible to be advanced through a straight lumen or sheath, but will regain the preformed arcuate or S-shape when present within the interior of the disc. The catheter should also be sufficiently flexible to conform to the shape of the disc wall, such as the posterior wall of the inner disc, when positioned against the wall. FIG. 10.

The S-shaped catheter allows the physician to treat the posterior wall, and particularly the lateral posterior wall, of a defective disc without the necessity of first contacting the anterior wall with the catheter. The device and process prevent the end or tip of the catheter from catching or hanging against the rough interior annular wall, which may have many crevices that make it difficult to advance the catheter along the wall. The S-shaped catheter allows the catheter to be introduced into the interior of the disc, and then positioned by manipulation of the introducer and catheter, without subjecting the catheter to being snagged by defects in the disc. The S shape facilitates good contact of the catheter with the postero-lateral segment of the disc even if the angle of the introducer entry is suboptimal. Additionally, the S shape retards the catheter traversing through any large segment of the interior of the disc which is typically filled with debris. This minimizes "shoveling" of the debris toward the segment of the inner annular wall to be treated.

Catheters may contain heating segments of various lengths. A final heating element, which is contained in each of these types of catheters, may be present directly at the tip, and is used for the spot sealing on exit from the inner annular wall. An additional embodiment has a straight catheter with a heating element at the tip.

On withdrawal of the catheter, the end or tip of the catheter straightens as it is exiting the annular wall. Spot heating at this position by tip 16 seals the defect that was created by the introducer and catheter.

Figure 12:
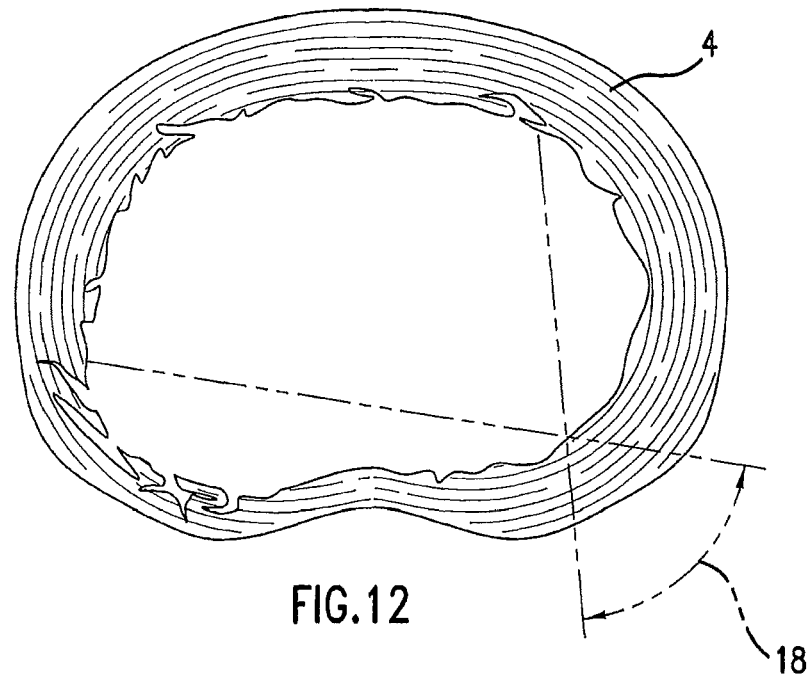
FIG. 12 demonstrates a range of permissive angles of insertion of the introducer relative to the disc.

FIG. 12 demonstrates an acceptable range of angles of introducer insertion 18 when driving the introducer into the disc. The acceptable range of angles is within about 70 degrees, but is not less than forty five degrees. Due to the S shaped configuration of the catheter, a precise entry of the introducer is not required.

Figure 13:
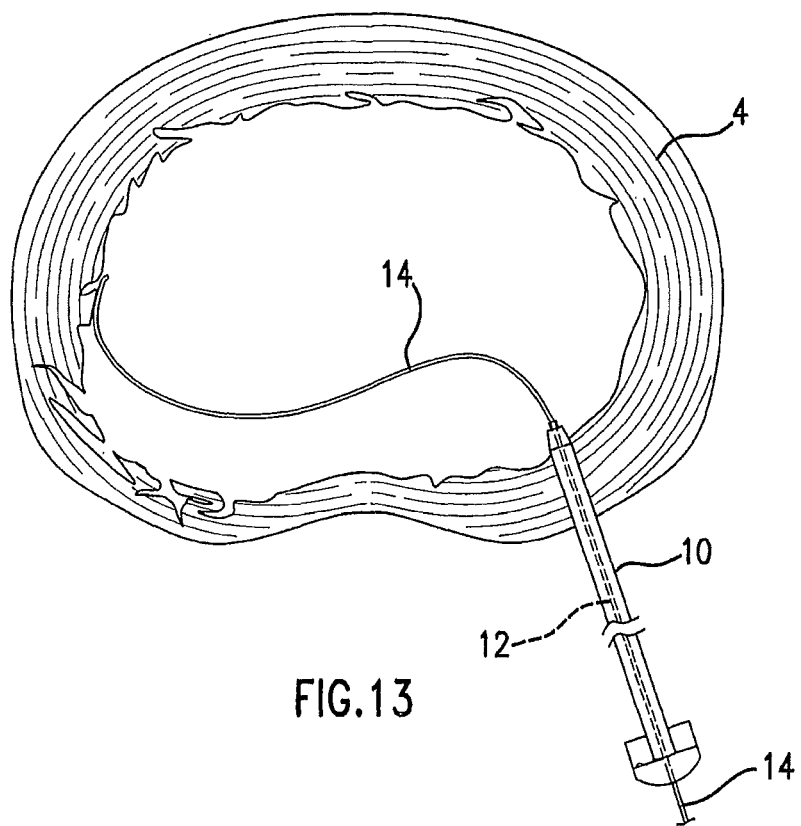
FIG. 13 demonstrates the introducer penetrating the annular wall at a different angle from that shown in FIGS. 5 through 11.
Figure 14:
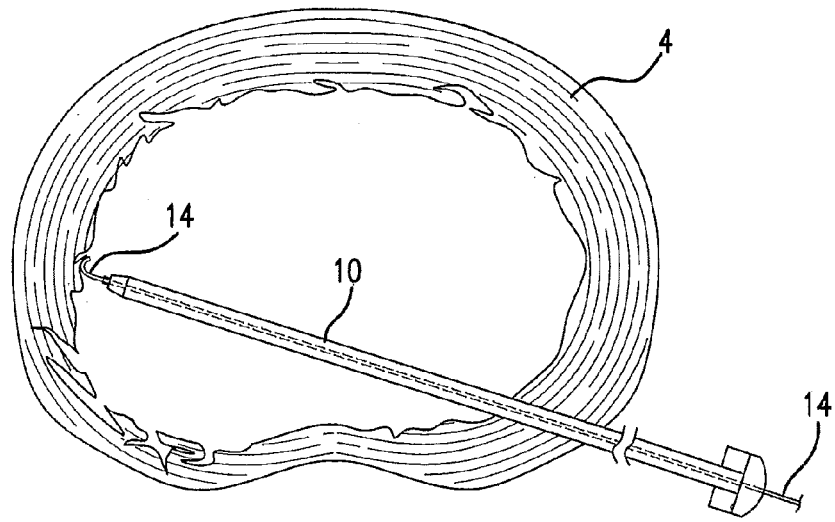
FIG. 14 demonstrates another angle of entry of the introducer into the disc.

As shown in FIG. 13, acceptable results are achieved with the S-shaped catheter used according to the novel method, even though the angle of insertion of the introducer varies from that shown in FIG. 10. Likewise, the angle of introducer insertion may be varied as shown in FIG. 14. The introducer may be withdrawn from the position shown in FIG. 14 to the interior, posterior annular wall, and S-shaped catheter is capable of being positioned against the lateral posterior wall of the disc by the method stated above.

Figure 15:
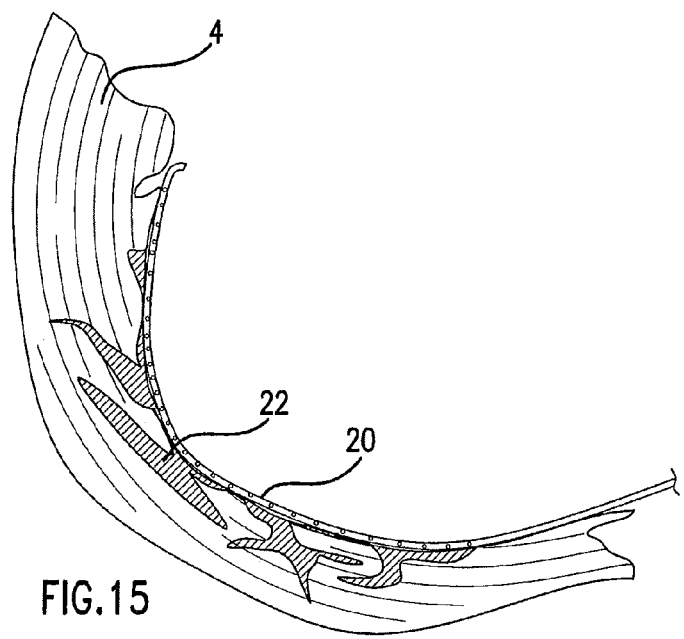
FIG. 15 demonstrates a catheter having multiple orifices therein through which materials may be dispensed.

The catheter may provide heat or radio frequency for the purpose of treatment of the disc. Other therapeutic applications may be used with the device and method. Further, a catheter 20 may have multiple orifices for the purpose of delivering materials such as adhesives, sealants or fillers into the disc. FIG. 15. A substance 22 may be injected through the catheter to the affected site to seal chemically, or otherwise, as opposed to thermally, defects including fissures and tears in the annular wall. Pressure manometery or fibro-optical viewing are also possible uses of this catheter system.

Figure 16:
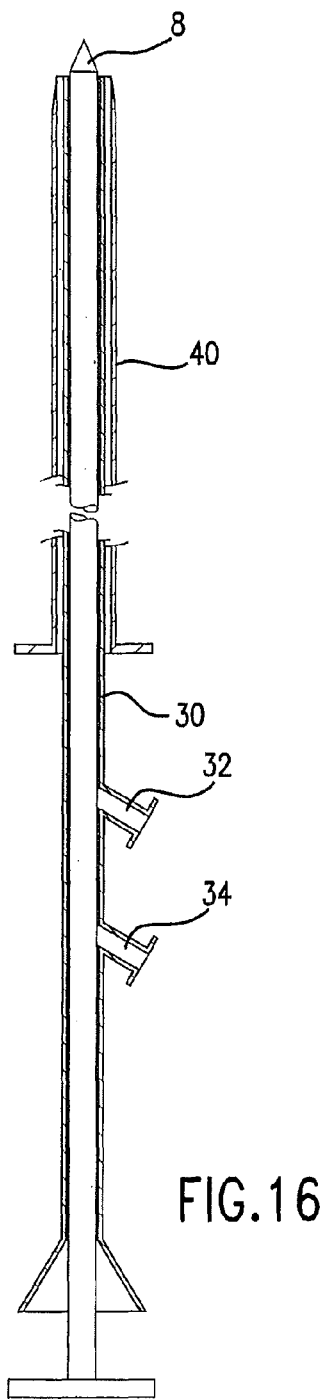
FIG. 16 is a sectioned view of an introducer inserted into a sheath having ports therein.
Figure 18:
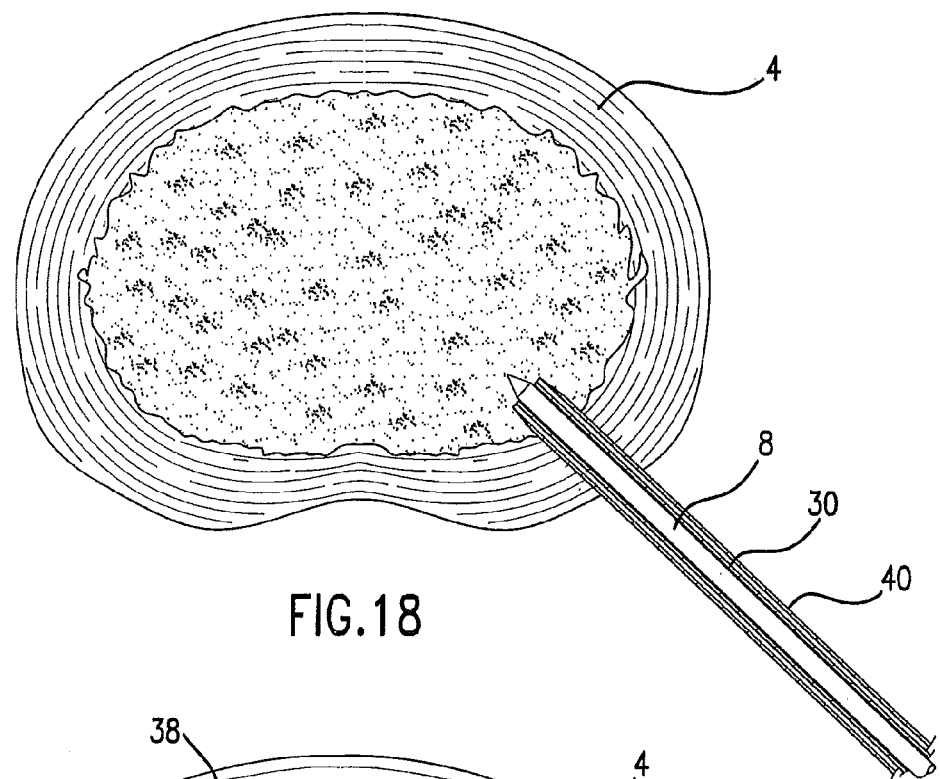
FIG. 18 demonstrates an introducer and stylet penetrating a disc.

FIG. 16 shows a second embodiment of the device, wherein the sheath has ports 32, 34 formed therein. The stylet is shown in position in the introducer of this embodiment. The stylet and introducer are used to access the interior annulus of the disc and shown in FIG. 18.

After entry into the disc, the stylet is withdrawn. The ports of the sheath may be used to insert materials into the disc, or remove materials from the disc. A vacuum may be applied to the ports for the purpose of removal of material.

Figure 19:
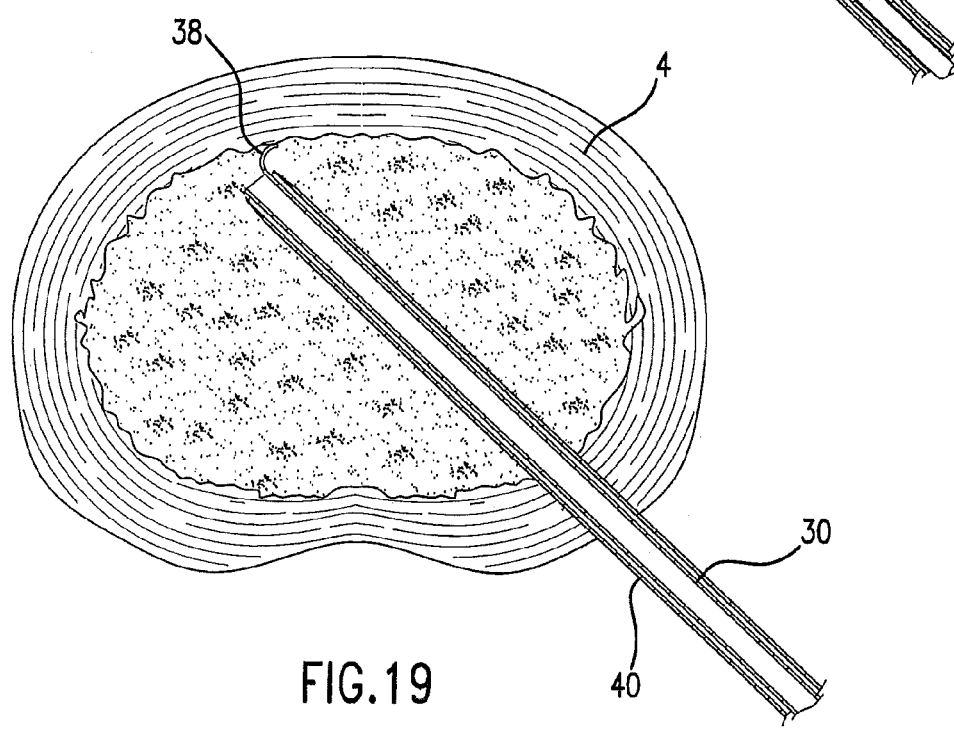
FIG. 19 demonstrates the flexible tip bending on contact with the inner annular wall.
Figure 20:
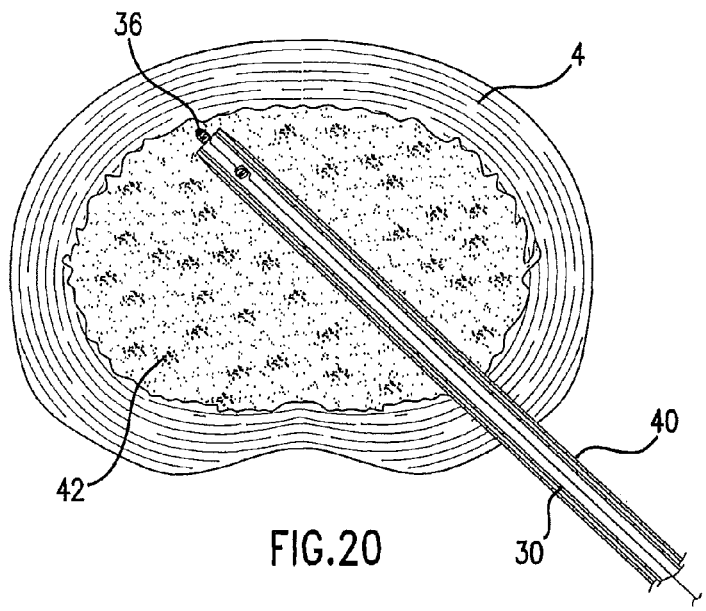
FIG. 20 demonstrates a cutter which may be used to remove material from the disc.

FIG. 19 shows a flexible deformable tip of the sheath. Deformation of the tip, which may be visualized fluoroscopically, defines hitting the inner annular wall. In one embodiment, 0.5 centimeters is sufficient protrusion of the sheath, such that it can be observed to bend when it contacts opposite inner annular wall. The bending of the tip of the sheath defines the limit of the inner annular wall immediately across from the entrance of the introducer complex into the disc. The limit of the inner annular wall opposite to the introducer insertion may be defined when fluoroscopically viewed.

Figure 17:
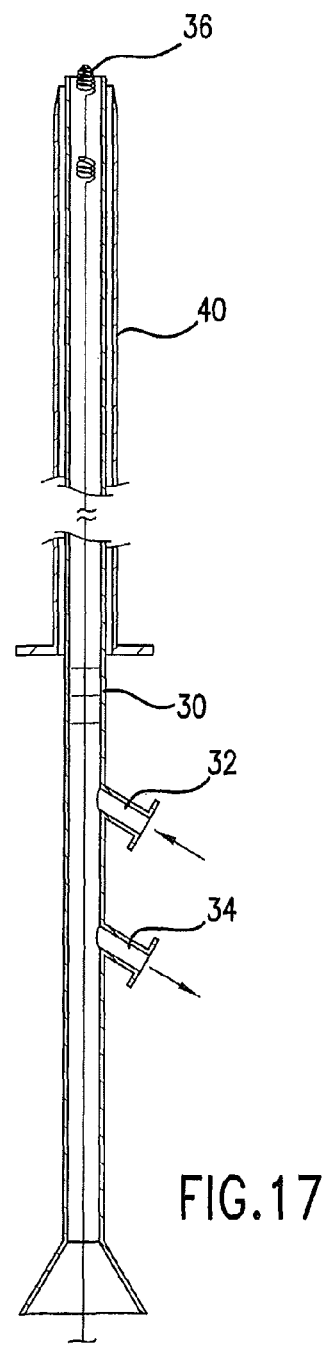
FIG. 17 is a sectioned view of an introducer having ports through which materials may be inserted into the disc, or from which materials may be removed, such as by vacuuming, and also showing a cutter therein.
Figure 21:
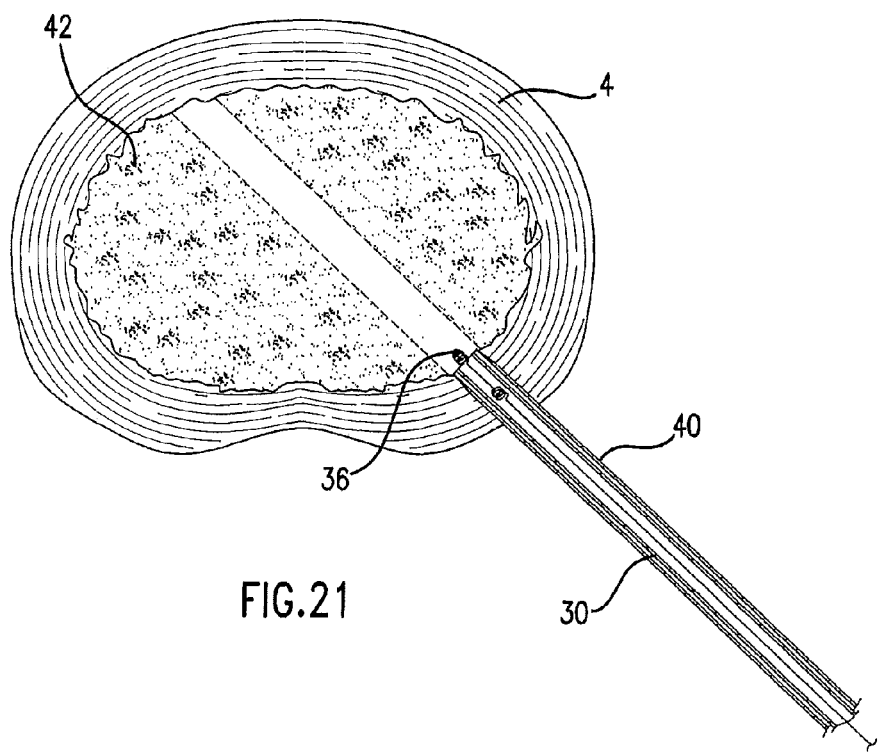
FIG. 21 demonstrates removal of a path of disc material using a cutter and a lavage/suction.

As shown in FIG. 17, a rotary cutter 36 is contained within the sheath. The rotary cutter is used to cut away material as the introducer is withdrawn. FIG. 21. Alternately, another type of cutter may be used.

When the introducer, sheath and cutter complex are in the nucleus, the tip of the flexible sheath is advanced by external manipulation such that it protrudes from the introducer. The threaded probe protrudes from the sheath, such as by 2-3 mm. The rotating threaded probe is activated to rotate within the inner annular wall. The initial "pass" of the rotating threaded probe is accomplished by withdrawing the introducer/sheath/probe linearly back to the position where the introducer/sheath tip is at the level of the opening into the inner annular wall as previously defined. The complex is then advanced back to its position at the opposite inner annular wall as previously defined fluoroscopically. The sheath/probe is kept in its current position while the introducer is withdrawn a pre-defined distance, such as 5 mm in one embodiment. The complex is again withdrawn with probe rotating. An additional amount of material is removed, similarly to mowing a lawn. If an additional amount of material is present between the first and second probe withdrawals, the amount of withdrawal can be modified to be less than, for example, 5 mm. In successive fashion, the complex is advanced, the introducer 40 withdrawn, the rotation of the treaded probe is started, the sheath/probe, and then the introducer segment, is withdrawn until the final sheath/probe withdrawal is accomplished with the introducer tip at the level of the insertional inner annular wall. Since the sheath is S shaped, short lengths of sheath protruded from the introducer will be arcuate. Incrementally longer segments of exposed sheath assume varying degrees of the S shape. This process very thoroughly evacuates the approximately half of the nucleus that is initially addressed. At this point, the sheath/probe is withdrawn into the introducer. The sheath/probe is rotated substantially 180 degrees within the introducer. The process is then repeated in the same fashion on the opposite half of the nucleus. Infusion of a substance, which could be normal saline, via a side portal 32 into the sheath, alternating with suction at portal 34, may be performed at intervals to facilitate removal of the nuclear contents.

Figure 22:
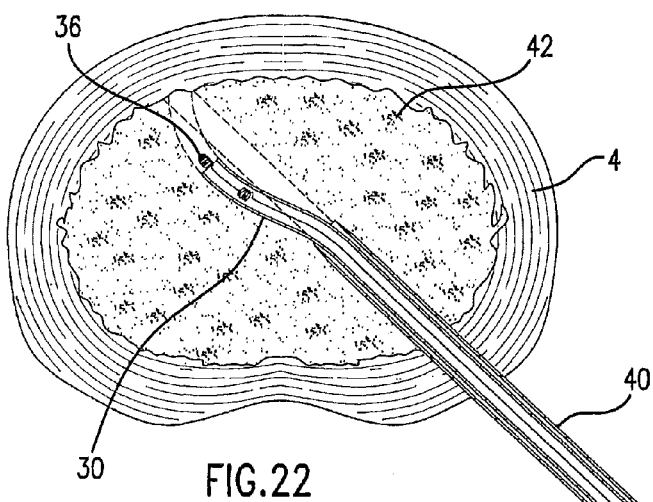
FIG. 22 demonstrates a progressive step in removing material from the disc.
Figure 23A:
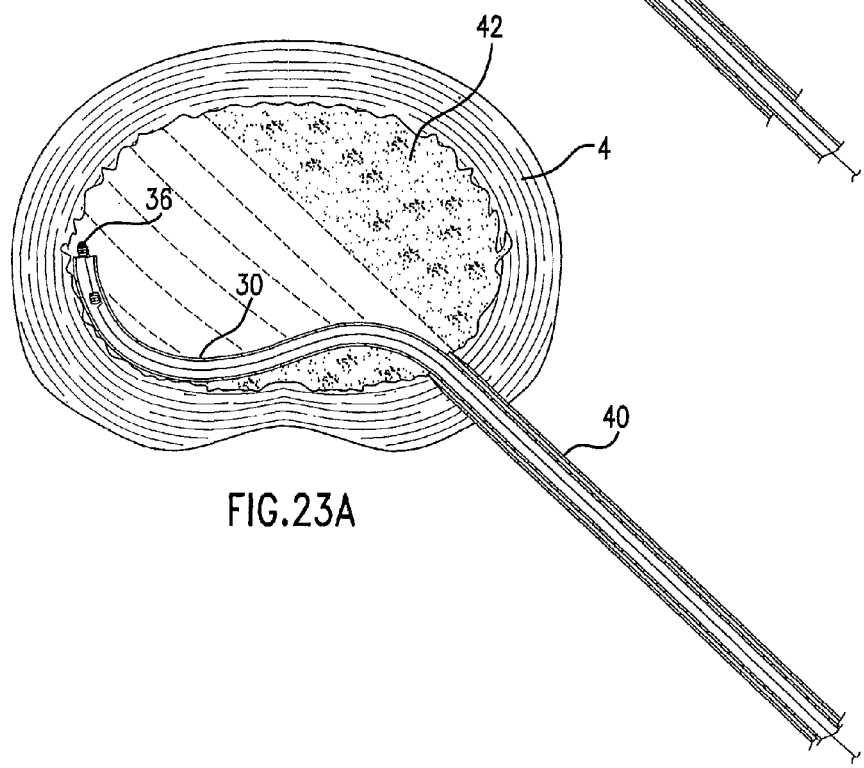
FIGS. 23A and 23B demonstrate an additional progressive step in removing material from the disc.
Figure 23B:
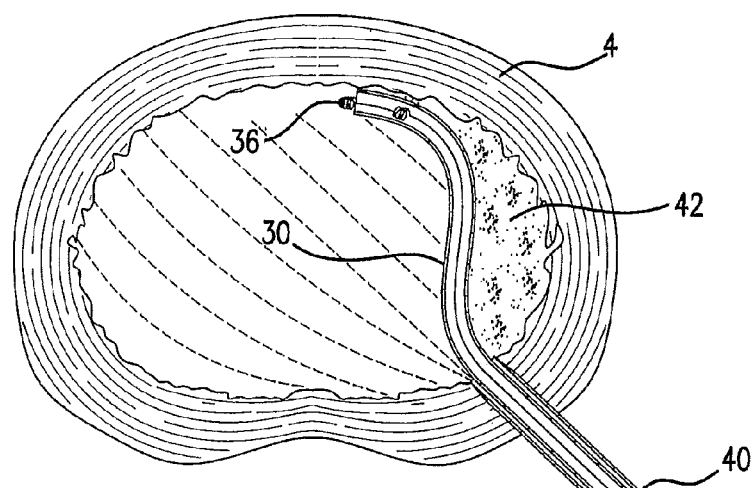

The sheath has a pre-formed S shape, and a memory for the S shape. Accordingly, as the rotary cutter is extended from the introducer, the sheath will continue to curve slightly, which allows material 42 which is adjacent to the cut taken in FIG. 21 to be removed. FIG. 22. As the rotary cutter cuts material away, lavage/suction are applied through the ports 34 of the introducer. One port allows for infusion of a substance (which may be normal saline) into one port. The other port is for suction or other form of removal of material including debris from the disc. By increasing the length of the S-shaped sheath from the introducer 40, additional passes each take material from the disc, as the cutter is further extended from the sheath. FIG. 23 demonstrates the cutter after the cutter has made six passes, and is beginning a seventh pass. In each pass, the arcuate shape of the sheath as it is extended which allows for progressively removing from the interior of the disc. Shorter segments of the sheath exposed from the introducer have an arcuate shape allowing for an infinite number of paths throughout the disc enabling the removal of nuclear material if needed.

Figure 24:
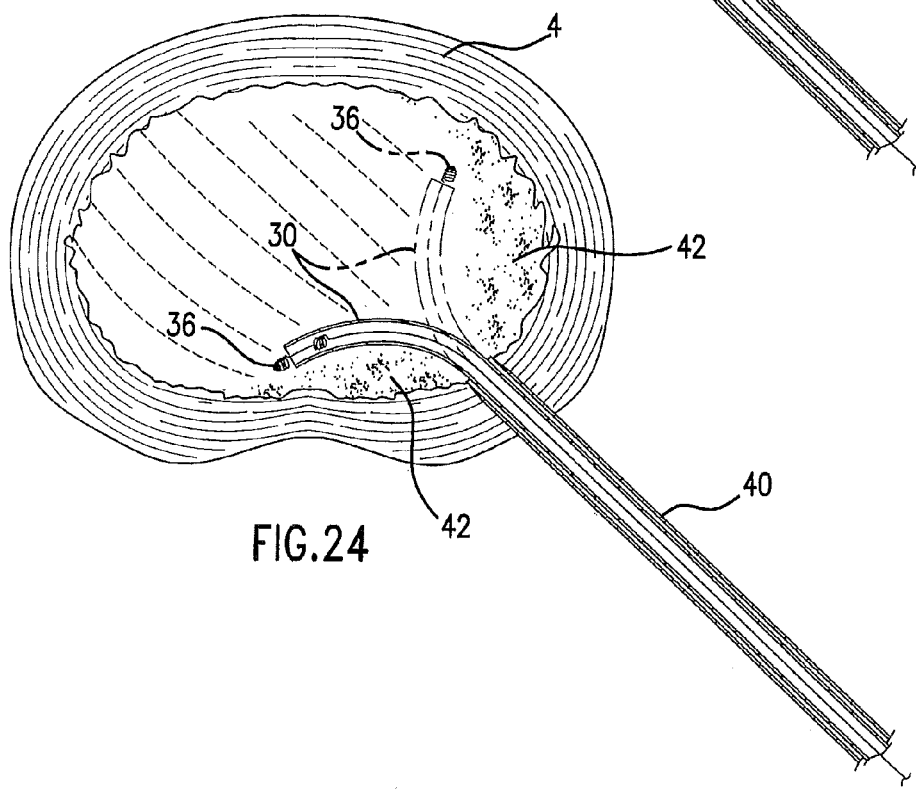
FIG. 24 demonstrates yet an additional step in removing material from the disc.

After the material is removed from one side of the disc, the cutter is retracted into the introducer. The cutter and/or the sheath are rotated 180 degrees, so that the S shaped cutter is present on the opposite side of the disc. The sheath containing the cutter is extended from the introducer on each subsequent pass as needed, until material is removed as desired from the disc as shown in FIG. 24.

Figure 25:
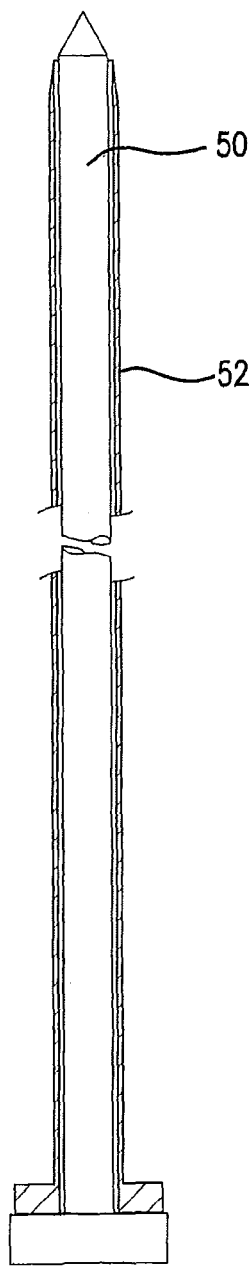
FIG. 25 is a sectioned view of an introducer with a trocar present therein.
Figure 26:
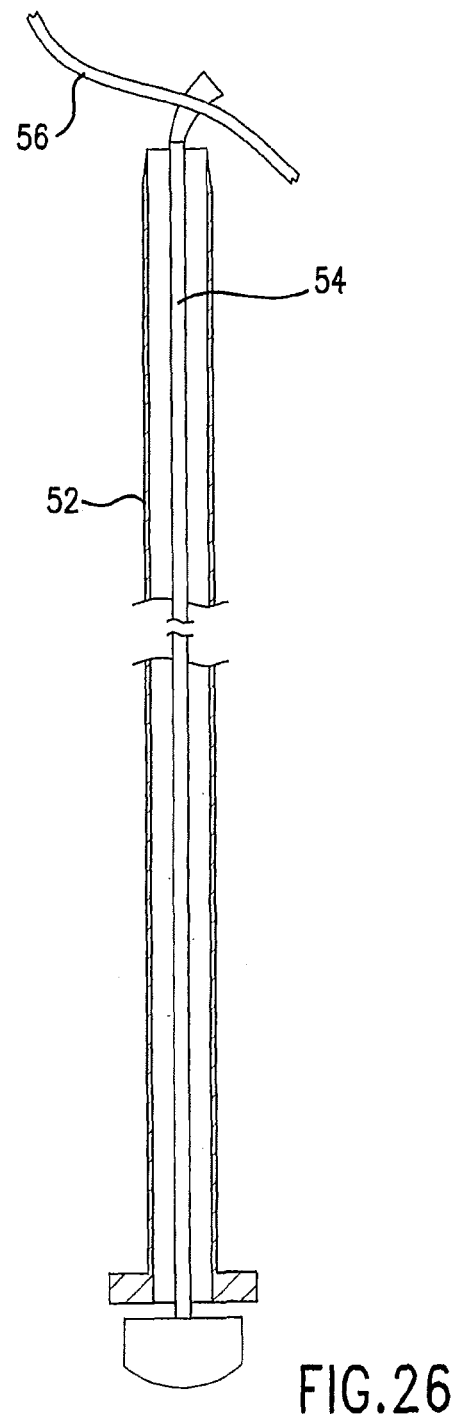
FIG. 26 is a sectioned view of the introducer with a retractor therein.

FIG. 25 shows a trocar 50 that is a present within an introducer 52. The trocar may be a relatively large stylet. FIG. 26 shows a retractor 54 that is present within the introducer. The retractor manipulates the nerve root 56.

Figure 27:
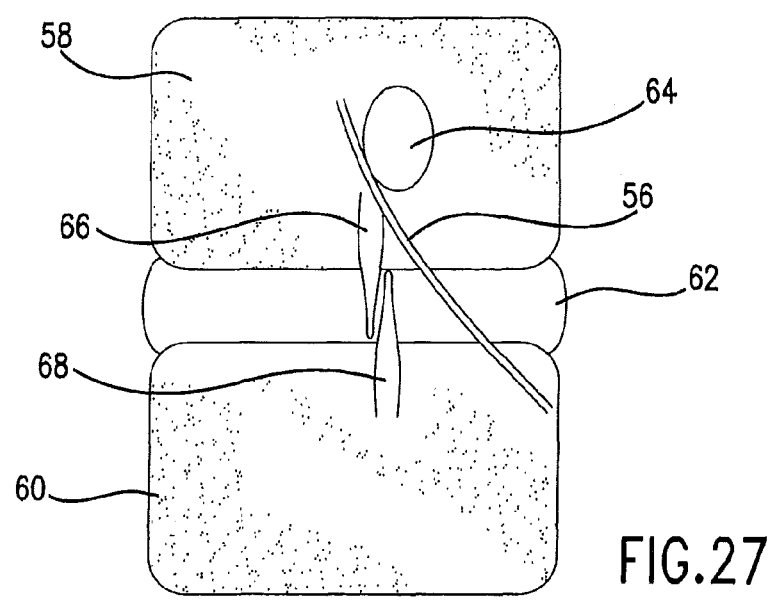
FIG. 27 is an oblique partial view of a mammalian spine.

FIG. 27 shows a vertebra 58 of a mammalian spine, an additional vertebra 60 of a mammalian spine, with an intervertebral disc 62 between the vertebrae. Also shown are a pedicle 64, a superior articular facet 68 and an inferior articular facet 66. The nerve root 56 is shown as traversing the intervertebral disc. As shown, the position of the nerve root interferes with access to the intervertebral disc. FIG. 27 is an oblique view demonstrating what is typically visualized flouriscopically for intradiscal procedures, except for the nerve root, which does not visualize under fluoroscopy, but whose position is known to an experienced operator.

Figure 28:
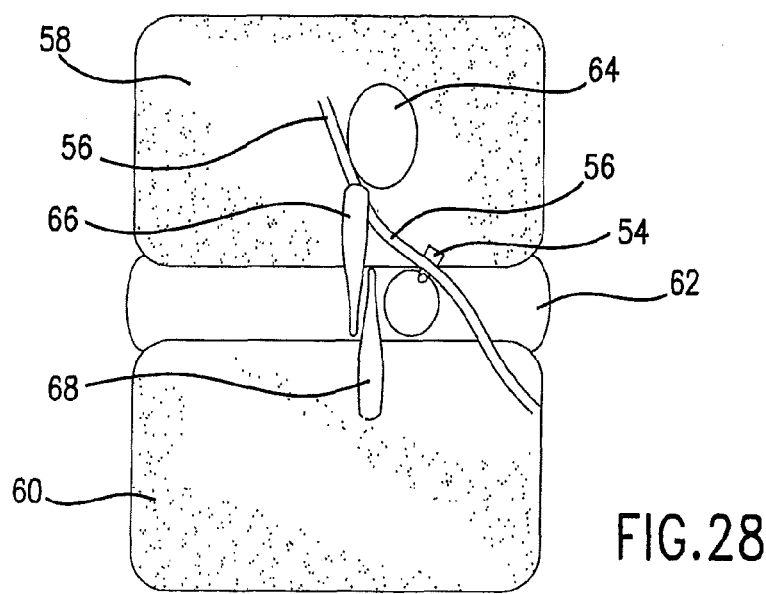
FIG. 28 is an oblique partial view of the mammalian spine with a retractor in position.

The trocar is used to pierce and penetrate skin and other tissue. Upon reaching the nerve root, the trocar is removed and the retractor is inserted. The retractor is used to lift the nerve root over the introducer, so that the nerve root is out of the way, and does not interfere with access to the intervertebral disc. FIG. 28.

Once the retractor has repositioned the nerve root over the introducer, the retractor may be removed from the introducer, and the trocar reinserted into the introducer. With the nerve root positioned over the introducer, the nerve root will not be damaged as the trocar and introducer are inserted into the intervertebral disc. The trocar pierces the intervertebral disc for access to the disc with the introducer.

Figure 29:
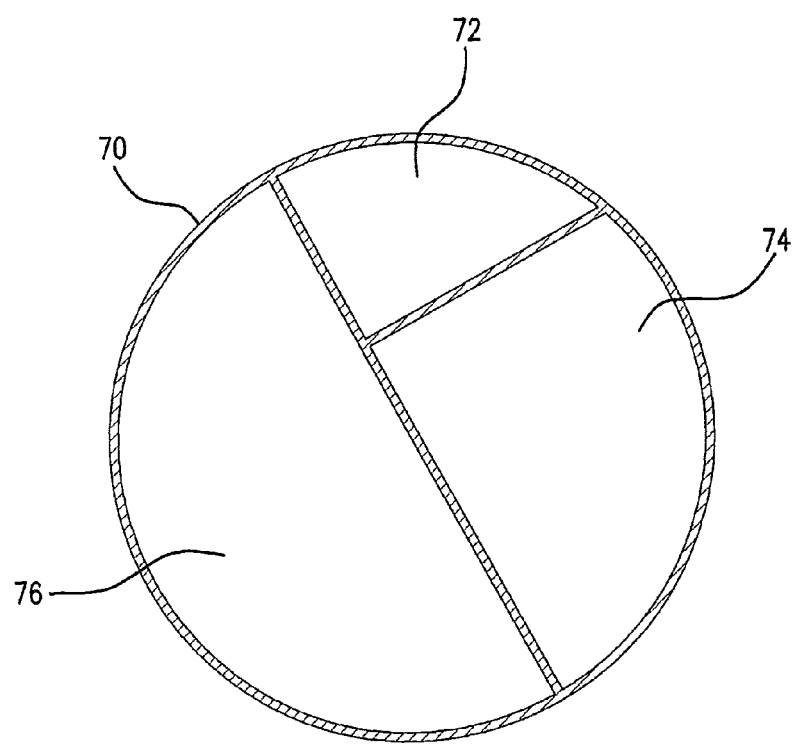
FIG. 29 is a sectioned view of a sheath.

FIG. 29 demonstrates a cross section of a sheath 70 that is used to evacuate a defective disc according to the method described. The sheath has three lumens in the embodiment shown. A first lumen 72 is used as a conduit for a fiber optic cable. A second lumen 74 is provided through which a cutter is delivered to the work site within the intervertebral disc. The cutter could be a laser cutter, or a mechanical cutter, such as a rotary cutter.

A third lumen 76 is relatively larger, and provides a conduit for levage and suction. Saline or other materials may be introduced to the work site in the disc through the lumen. Tissue that is removed, along with attendant blood and other materials, may be suctioned and evacuated through lumen 76.

Figure 30:
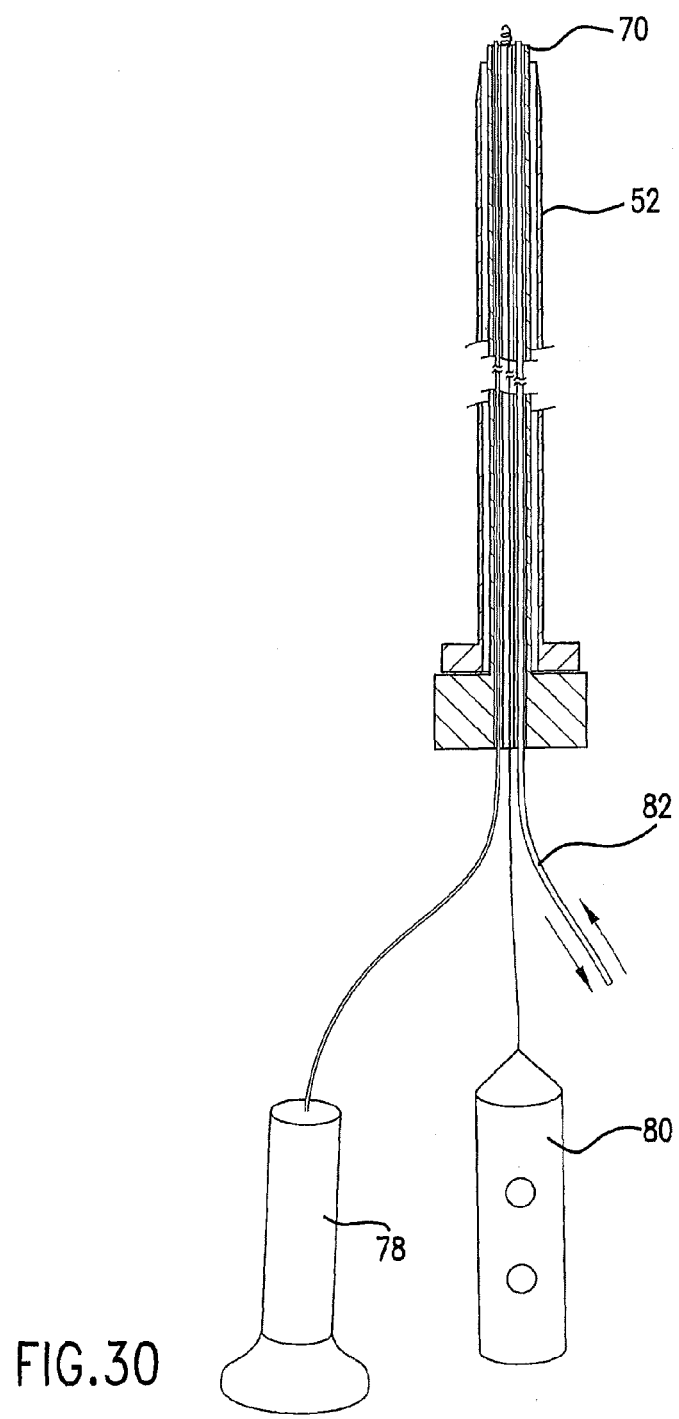
FIG. 30 is a sectioned view of a sheath and introducer with a cutter, fiber optic source and lavage and suction in place.

FIG. 30 shows the fiber optic source 78, cutter 80 and the conduit for levage and suction 82.

Figure 31:
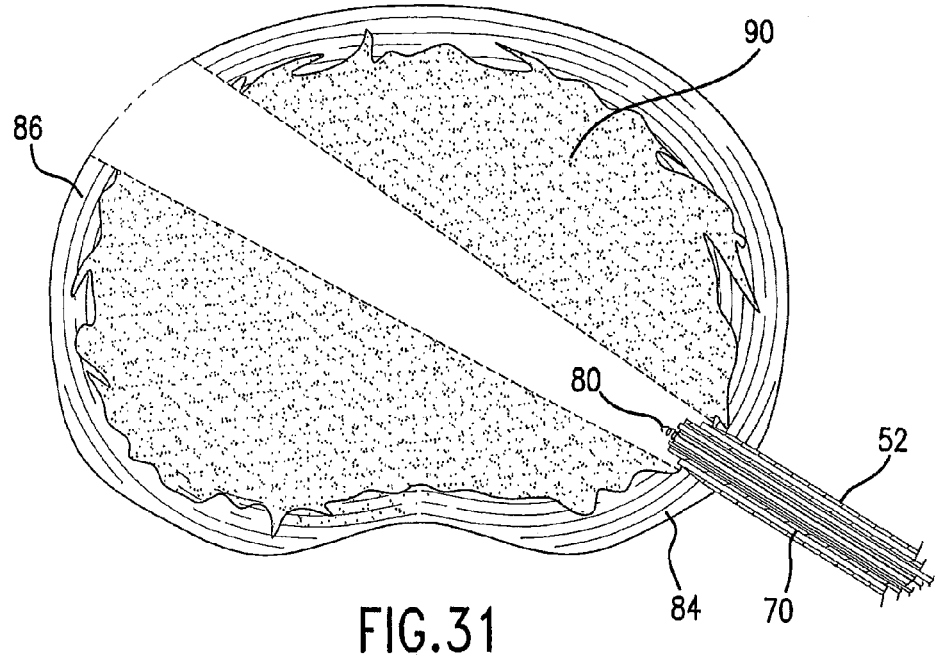
FIG. 31 is plan view of a mammalian intervertebral disc showing a portion of the disc evacuated according to the method of the invention.

The introducer penetrates the wall of the disc as described above. The introducer is shown as having penetrated the lateral posterior wall of the disc 84 in FIG. 31. The sheath is positioned within the disc through the introducer. The sheath is initially positioned so that its forward end extends only slightly beyond the end of the introducer. The cutter, the fiber optic and the levage and suction are actuated, and the entire assembly, along with the introducer, are pushed to the opposite wall 86 of the disc, which in this case, is the lateral anterior portion of the disc so that the pulposa of the disc and the disc wall itself are removed, as shown in FIG. 31. Since the materially extended sheath has an S-shape when no pressure is applied to the sheath, there will be a slight curvature of the sheath as it marginally extends from the introducer. Accordingly, the cut as shown in FIG. 31 is somewhat conical in shape, rather than being straight, due to the arcuate shape of the sheath when the sheath is advanced slightly from the introducer.

Figure 32:
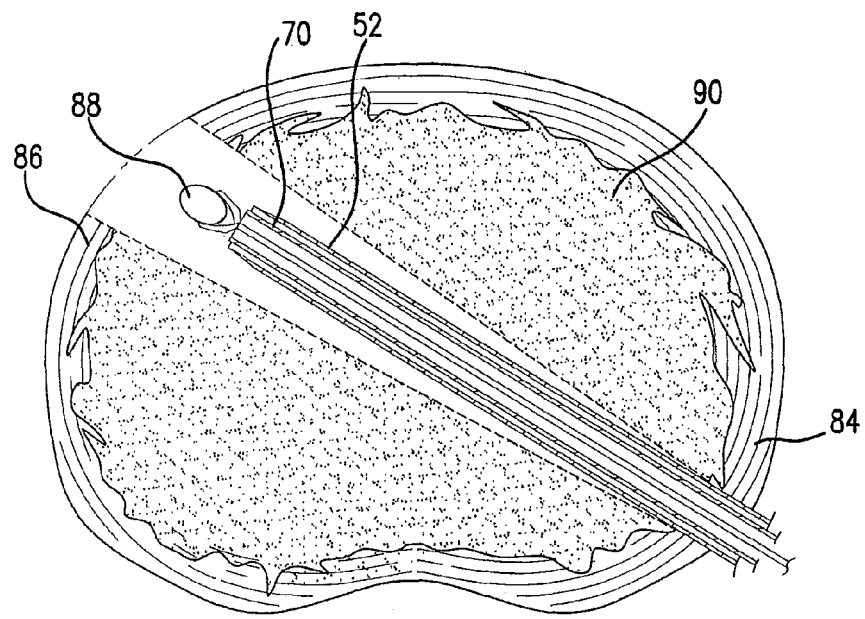
FIG. 32 shows placement of a support member within the intervertebral disc.

As the intervertebral disc is removed, support must be provided for the adjoining the vertebrae. FIG. 32 shows the cutter removed from the sheath, and a support member or strut 88 placed in position using insertion or placement tool. The support member or strut may be capable of inflation using, for example, saline. Accordingly, the support member or strut may be a solid, a balloon or bladder.

Figure 33:
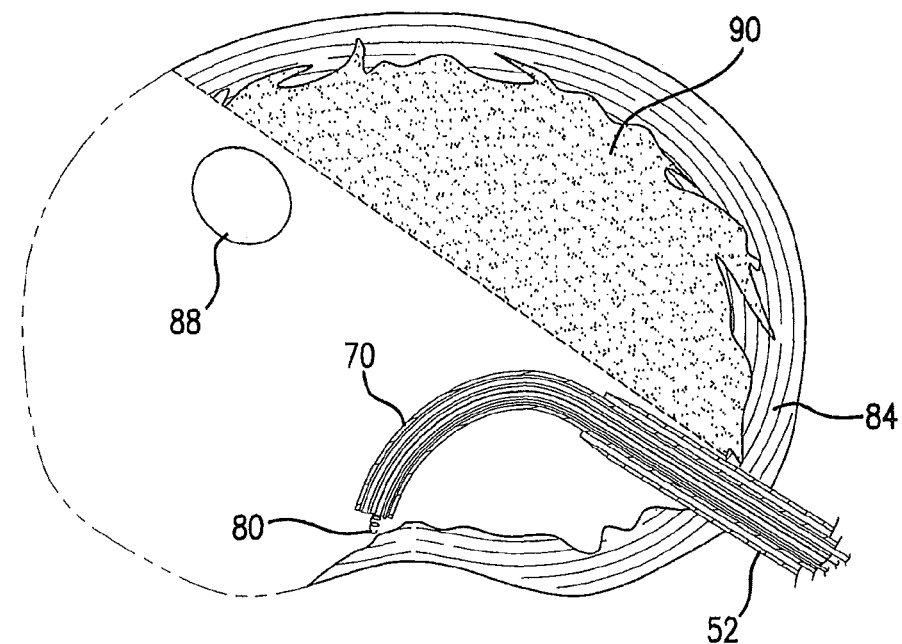
FIG. 33 shows a progressive step of the disc being evacuated according to the method of the invention.

The sheath is progressively extended, and progressive cuts are made using the cutter or other tool to traverse in and out of the disc. As shown in FIG. 33, progressive cuts are made until the disc and associated pulposa 90 are partially or totally removed from one side of the sheath. The cutter may be removed from the sheath as required, and the placement tool inserted for placement of the support members or struts within the intervertebral disc.

Figure 35:
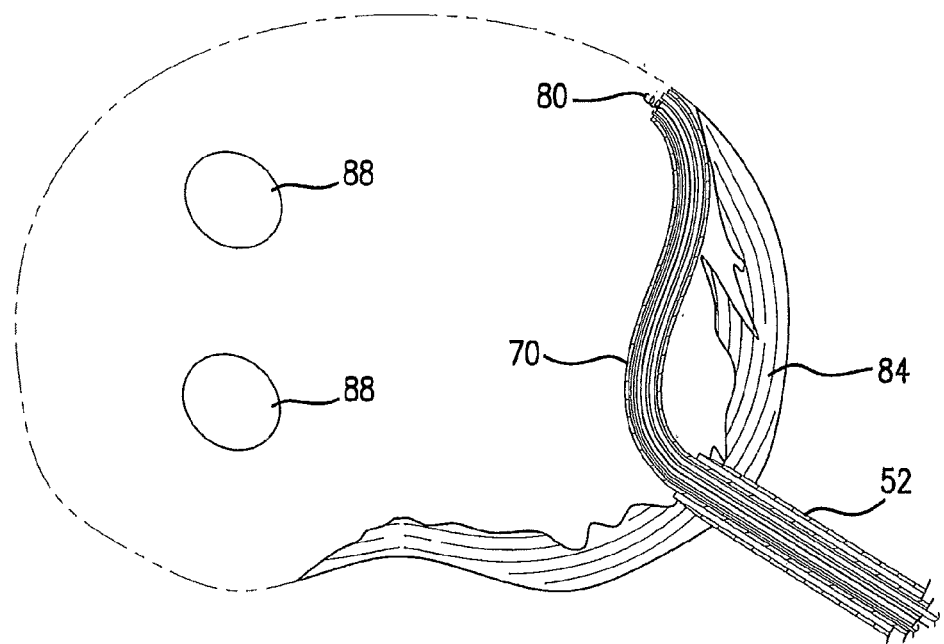
FIG. 35 shows an additional progressive step of the disc being evacuated according to the method of the invention.

After one side of the disc is substantially removed, the sheath, and/or the introducer and sheath, are rotated 180 degrees. FIG. 35. The cutter is in position in the sheath. Additional progressive passes are made by steering and advancing the introducer and sheath, individually, or as a unit within the disc, and with the cutter in place.

The-sheath permits the material of the disc which is offset to each side of the introducer to be removed, even though the sheath is advanced and retracted on what is generally a straight line dictated by the void formed in the disc through which the introducer passes. The sheath allows the cutter to reach progressively laterally as the sheath is progressively extended from the introducer. The sheath of this embodiment, and the catheter shown in FIG. 4 through FIG. 15, and the sheath shown in FIG. 23 through FIG. 24, each have an S-shape when no material pressure is applied to the catheter or sheath. The catheter or sheath in each embodiment of the invention shown herein has a memory property which returns the catheter or sheath to an S-shape when no material pressure is applied to the catheter or sheath. However, when the catheter or tool is present within the sheath, or in the case of the catheter, within the sheath for the catheter, the S shaped element is reformed to be straight, but regains it S shape as it exits the straight lumen. The sheath is preferred to be straight, and in some embodiments, rigid when used with an S-shaped catheter or tool having memory.

Figure 37:
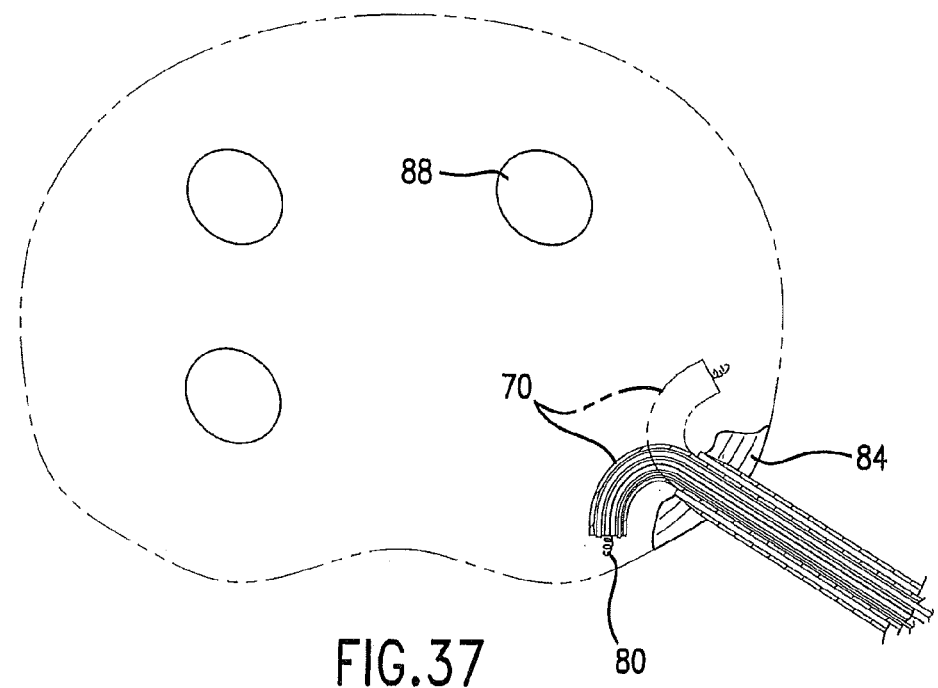
FIG. 37 shows an additional progressive step of the disc being evacuated according to the method of the invention.
Figure 38:
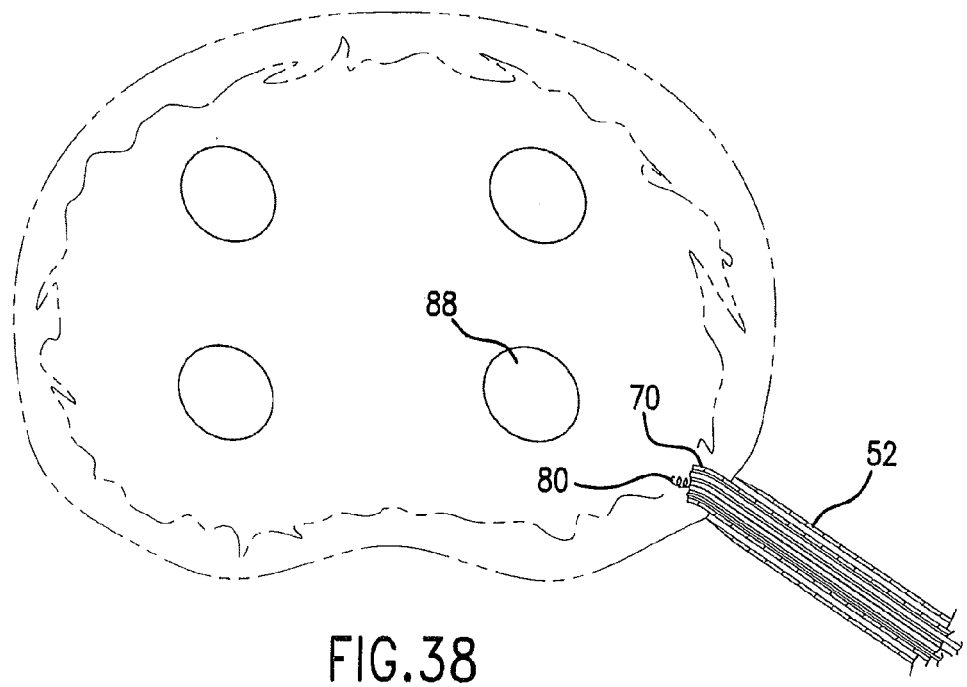
FIG. 38 shows an additional progressive step of the disc being evacuated according to the method of the invention.

Continuing with the process of this preferred embodiment as shown in the drawings, FIG. 37 demonstrates the final cutting away of the disc by slight protrusion of the sheath from the introducer. FIG. 38 uses the cutter with the cutter even more slightly extending from the introducer to remove the disc. Although it is possible to remove the entire intervertebral disc, it may be desirable to leave some of the intervertebral disc in place as a support, as long as the targeted defective portion of the intervertebral disc is removed by the method described herein.

Various materials may be positioned within the intervertebral disc as well as within the vertebral body using the S-shaped tool. The S-shaped tool, when used in combination with the introducer as taught herein, allows the material to be positioned about the interior wall of an intervertebral disc or a vertebral body, or within the interior of the disc or body, as desired. Materials that are useful in treatment or diagnosis of the spine may be positioned using the device and method according to the invention. Such materials include, but are not limited to, epoxies, cements, gels, balloons, artificial discs, and artificial nuclei. The materials may include biological materials, such as regenerative materials that induce re-growth of spine tissue. Regenerative materials that may be positioned in the disc or vertebral body and may include morselized bone, bone substitute, or such materials as bone morphogenic protein.

Figure 34:
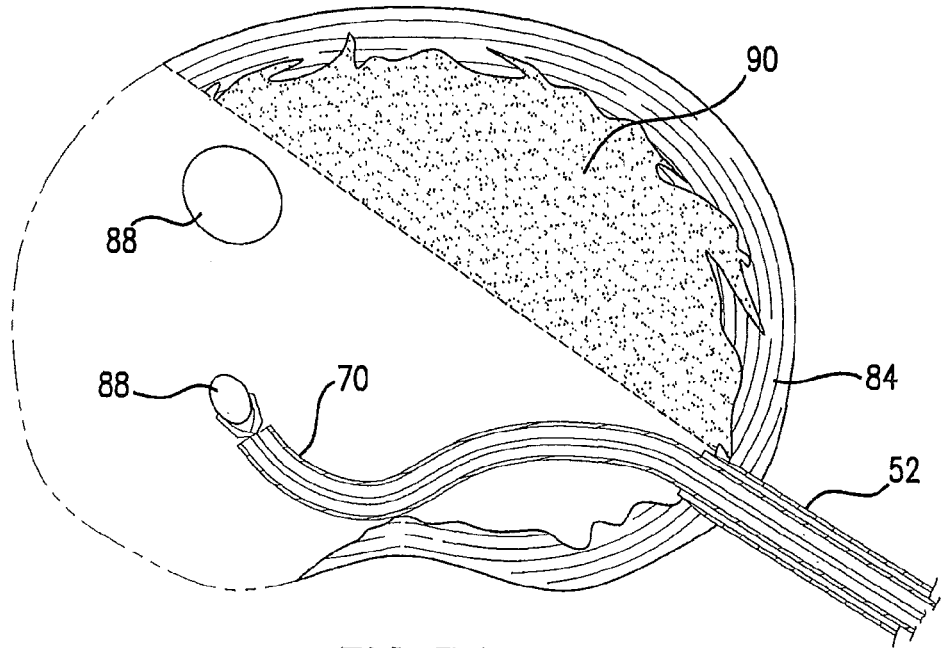
FIG. 34 shows an additional support being positioned within the disc.
Figure 36:
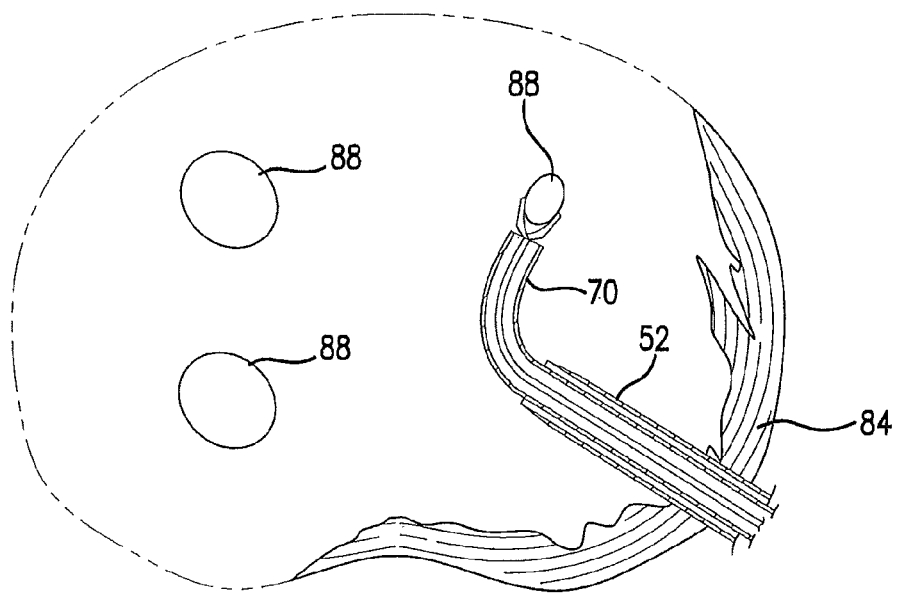
FIG. 36 shows an additional support being positioned within the disc.

Materials may be positioned inside the disc or body by tools having a lumen that provides a conduit through which fluids, including gases, liquids, gels, and semi-solids, may be transported. Materials having elastic properties, such as balloons, may similarly be transported and inflated within the disc or vertebral body. Materials having a solid structure may be positioned by tools that allow for grasping and releasing the material, such as forceps, or the placement tool shown in the drawings. FIGS. 34 and 36. The interior of the intervertebral disc and the vertebral body may be accessed as disclosed herein, or by known methods.

In one embodiment, regenerative material is placed in the space created by evacuation of the disc. The regenerative material may be positioned prior to, in conjunction with, or after, positioning of the spacers or struts 88 as described above. The regenerative material will take time to create new tissue. If used, the spacers or struts maintain a space for the tissue. The regenerative material may be placed by the elongated tool as taught by the invention or otherwise inserted or injected. A tamp may be used to pack the material.

Material may be used to provide support for the spine where elements of the spine, such as when some or all the disc or the vertebral body has been removed, or when these elements have suffered disease or damage. Placement of material may be performed by the elongated S-shaped placement tool according to methods described herein. Such filler or support material may be solid, regenerative material, gel, balloon material, struts, cements or other filler materials. Disc replacement devices and materials may be positioned by the elongated S-shaped placement tool. Spinal fusion processes may also be performed, with fixation devices and materials placed. This part of the process may, or may not, require the tool to be S shaped.

Figure 3:
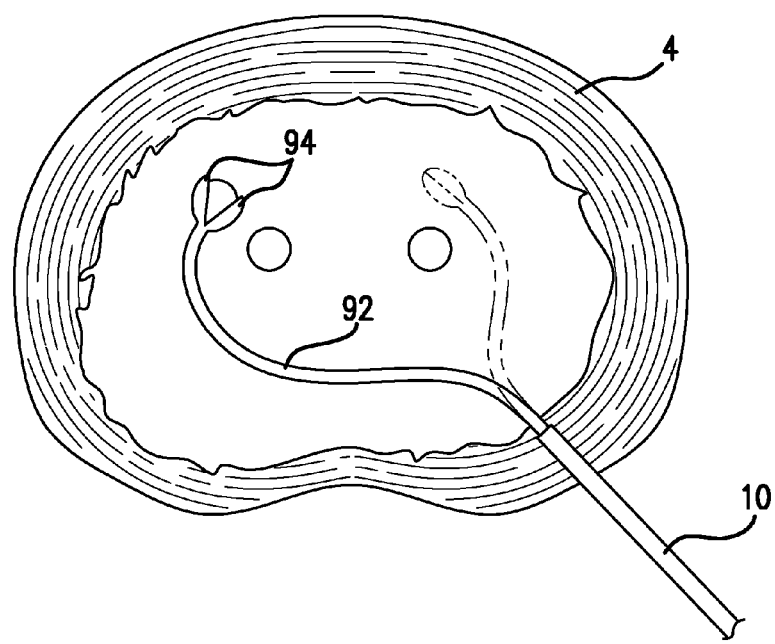
FIG. 3 demonstrates a device for placing material or objects and removing material or objects and positioned within an intervertebral disc or vertebral body.

FIG. 3 shows a tool positioned at the end of the S-shaped tool 92 that is useful for placing material, such as medicaments, spacers or struts, or regenerative material. This tool may also be used for removing objects, tissue, or material. In one embodiment, the tool has opposing spoons 94 or scoops that form a clam shell device. The user manipulates the opposing spoons or scoops to grasp and release material or objects. The spoons or clam shell may be manipulated from an external position by the user through an actuator traversing the elongated portion of the tool and/or the sheath that extends to the exterior of the disc 4.

Figure 39:
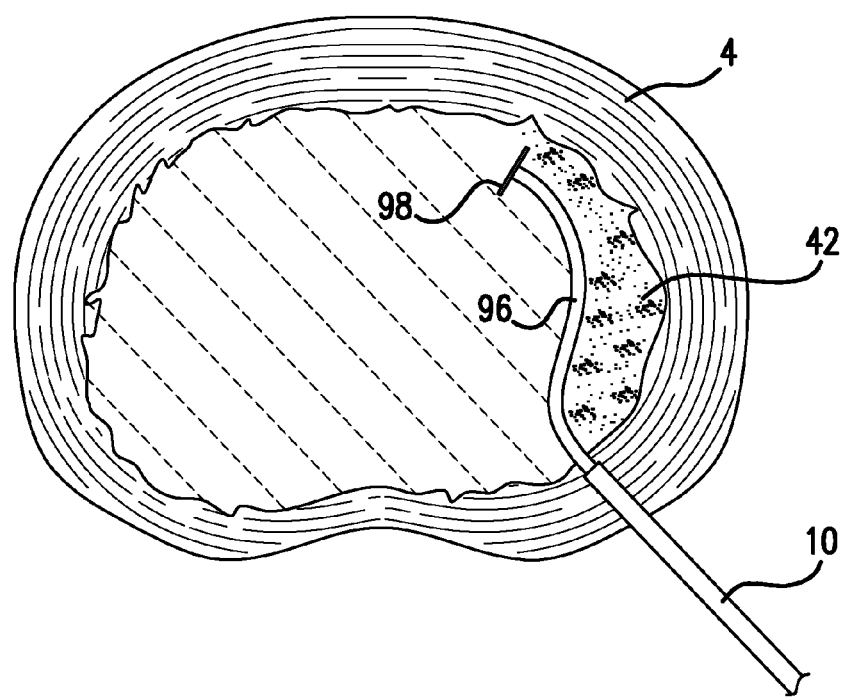
FIG. 39 demonstrates a device for removing material or objects and from a vertebral body or intervertebral disc.

FIG. 39 shows a tool positioned at the end of the S-shaped tool that is useful for cutting and removing objects, tissue or material. The tool has a blade 98 at an end of the S-shaped tool 96. The blade may have a sharp edge, like a razor, or the blade may comprise longitudinal fingers that extend away from a central member, like a rake. The blade may be manipulated from an external position by the user through an actuator traversing the elongated portion of the tool and/or a sheath that extends to the exterior of the disc 4. Tissue 42 or other material that is harvested by the tool may be evacuated, such as by suction. The suction may be provided through the tool and/or through a sheath.

Figure 40:
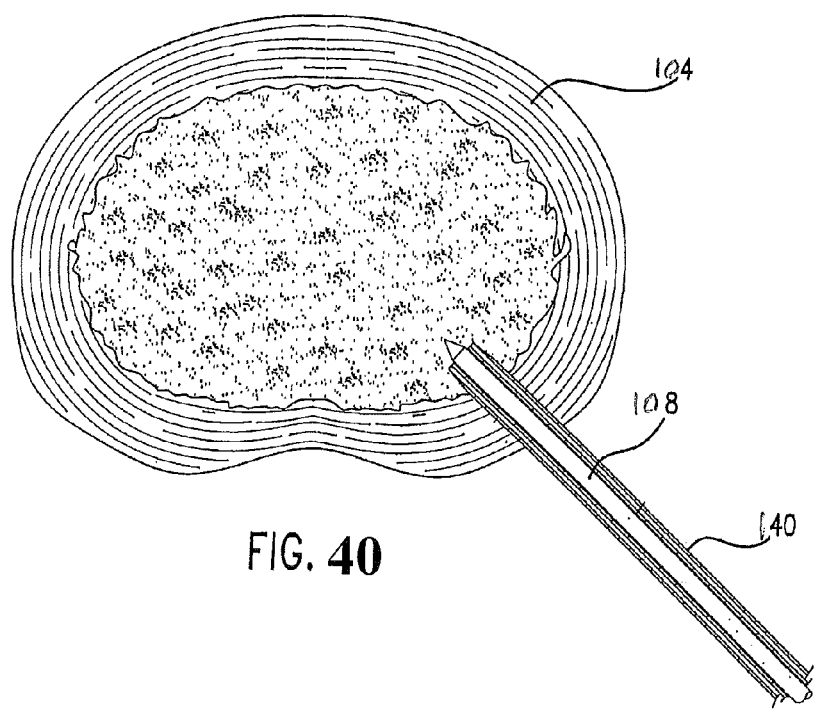
FIG. 40 demonstrates an introducer and stylet penetrating a disc.
Figure 41:
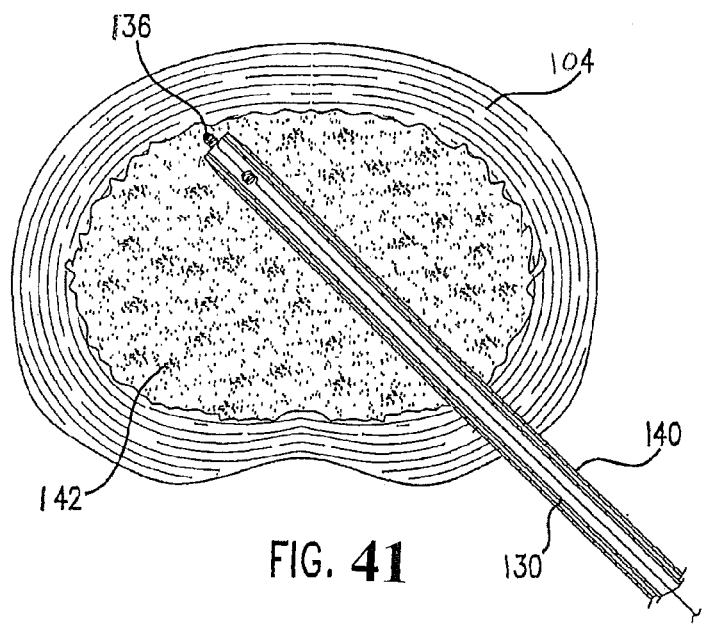
FIG. 41 demonstrates a cutter which may be used to remove material from the disc.
Figure 42:
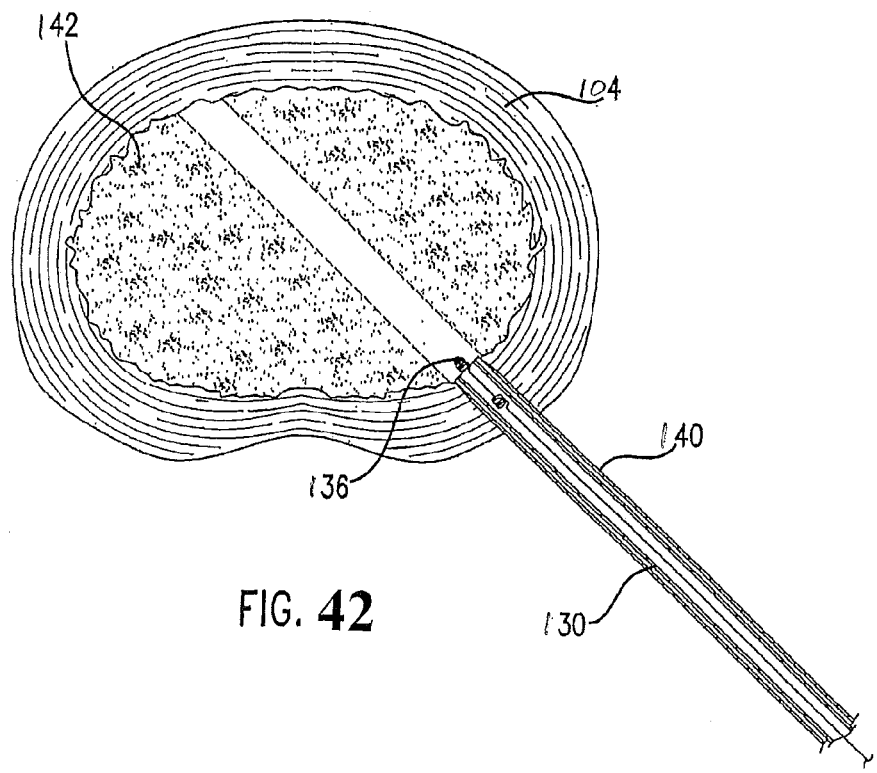
FIG. 42 demonstrates removal of a path of disc material using a cutter and lavage/suction to remove material.
Figure 43:
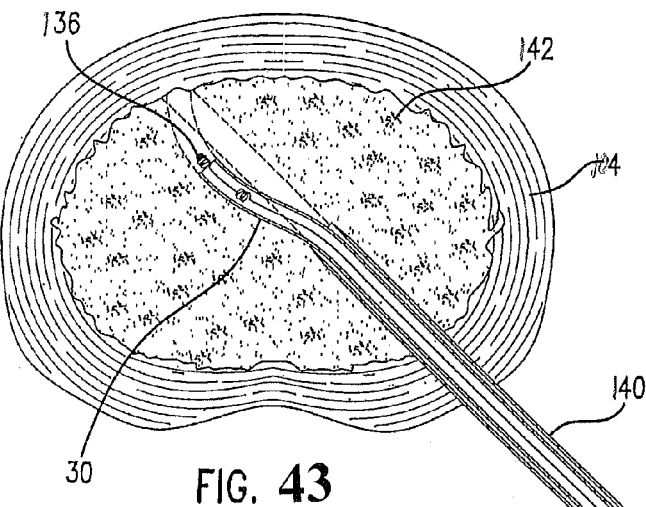
FIG. 43 demonstrates a progressive step in removing material from the disc.
Figure 44:
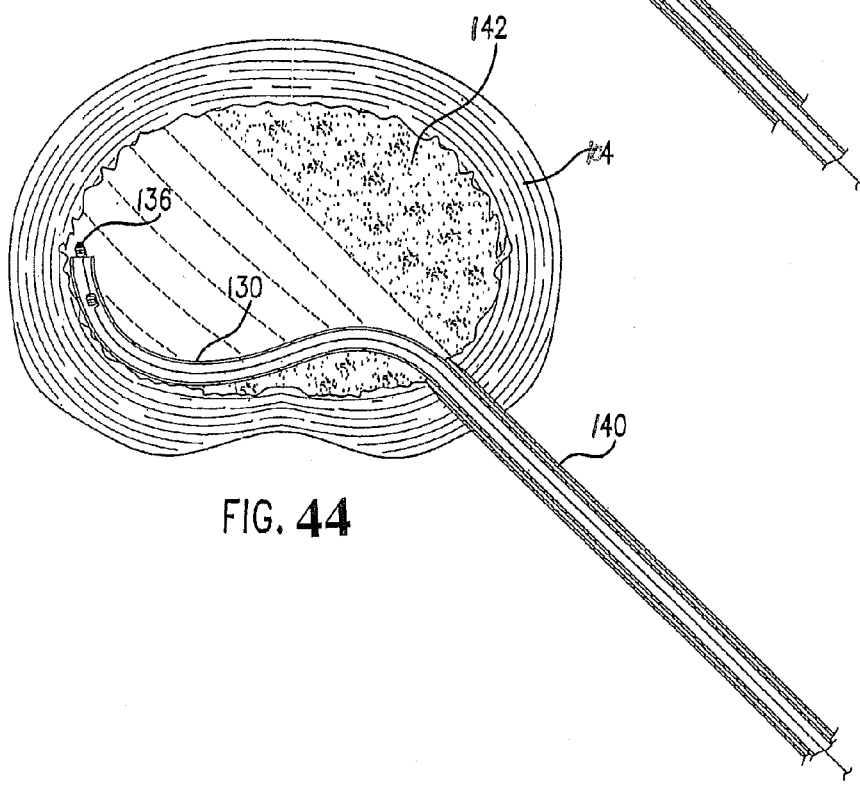
FIG. 44 demonstrates an additional progressive step in removing material from the disc.
Figure 45:
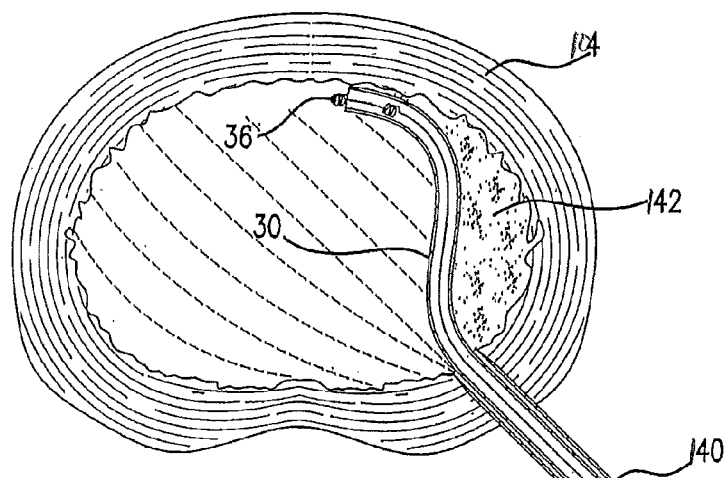
FIG. 45 demonstrates yet an additional step in removing material from the disc.
Figure 46:
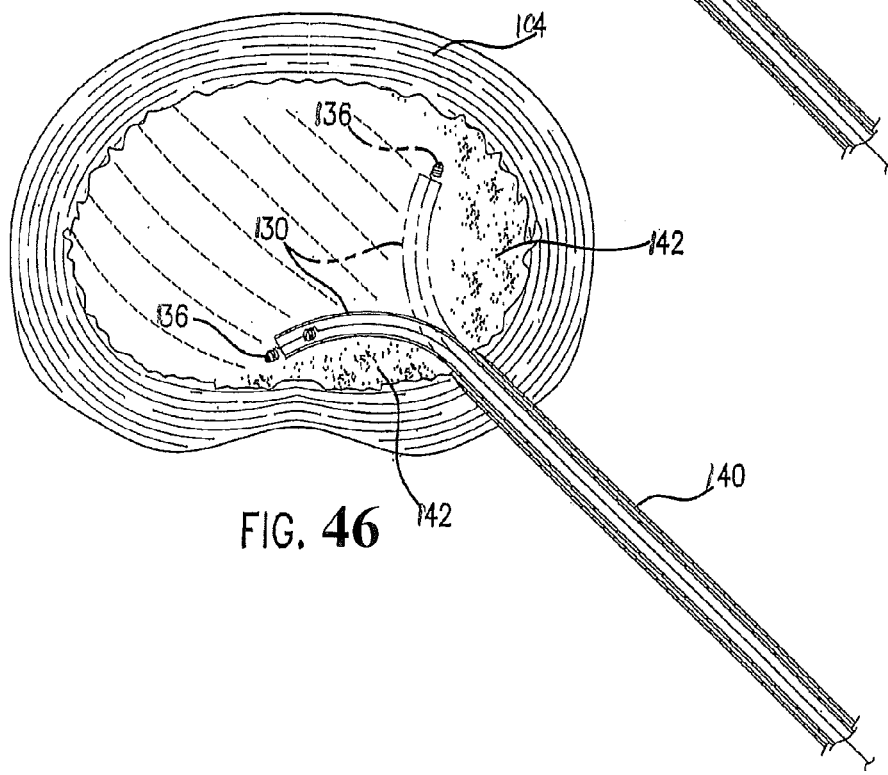
FIG. 46 demonstrates a further step in removing material from the disc.

Fusion of intervertebral bodies may be performed according to another embodiment of the invention. The invention permits a posterior, postero-lateral, or lateral approach to the disc and/or intervertebral bodies. In one embodiment, a small incision is made, which is preferred to be 30 mm or less. An introducer 108 penetrates the wall of the disc 104 through the incision for a direct posterior, postero-lateral or lateral approach to the spine. FIG. 40. In one embodiment, the introducer is present within a sheath 140.

After penetration of the intervertebral wall, the introducer is removed. According to one embodiment, the sheath 140 remains in the disc, penetrating the void formed in the disc wall by the introducer. An S-shaped tool 130 according to the invention is transported through a lumen in the sheath. The S-shaped tool is deformable, according to the invention as described herein, and assumes the shape of the lumen of the sheath. In most embodiments, the lumen of the sheath will be straight, and the S-shaped tool generally assumes the straight form. In another embodiment, the S-shaped tool is formed by and contained within a second sheath, and the second sheath and tool are transported through the lumen of the first sheath into the disc.

The S-shaped tool exits an end of the first sheath that is distal to the surgeon or other operator. The S-shaped tool reassumes or regains its S-shaped curvature as it exits the lumen of the first sheath in the interior of the disc. In this embodiment, the S-shaped tool is used to minimize the inner contents 142 of the disc for removal of the contents. If desired, the surgeon or other operator may also remove portions, or all, of the annulus of the disc.

The S-shaped tool may be or may comprise a grinder 136 or similar tool that minimizes the inner contents of the disc by the application of mechanical force to the contents of the disc. Alternatively, energy may be used to assist in minimizing the contents of the disc. Without being bound by theory, a laser, heat or radio frequency may be useful in minimizing the tissue, and such devices may be delivered by the S-shaped tool.

The elongated tool 130 comprises shape memory properties, so that the tool can be formed for transport through the guide or lumen of the sheath. The elongated tool regains its S-shape upon exiting the lumen of the sheath. The sheath 140 and the elongated S-shaped tool 130 may be manipulated independently of each other to advance and retract the sheath within the disc or vertebral body, and to expose as much of the S-shaped tool as is required relative to the sheath. As with the embodiment shown in FIGS. 20 through 24, after material is removed from approximately half of the nucleus of the disc, the cutter and/or the sheath may be rotated up to 180 degrees, or more, as needed, so that the S shaped cutter is present on the opposite side of the disc. The elongated S-shaped tool may thereby be positioned as desired within the disc or the vertebral body. The elongated S-shaped tool allows precise positioning of the tool. The device progressively removes material as shown in FIGS. 41 through 46, if progressive removal is required.

The elongated S-shaped tool also allows gross positioning of material where precision placement is not required. The sheath 140 is acting as the introducer of previously discussed embodiments.

After the disc, or contents of the disc, is satisfactorily minimized by the S-shaped tool, and, if used, the second sheath, are withdrawn, and removed from the disc and from the first sheath. If relatively large pieces of the interior of the disc remain within the interior of the disc, a second S-shaped tool 170 is transported through the first sheath 140. The second S-shaped tool may also be transported through the first sheath along with a second sheath that contains the second S-shaped tool. The second S-shaped tool comprises a device for grasping pieces of the disc that have been separated by the first S-shaped tool. The tool 172 for grasping these particles may be devices having opposing jaws that are manipulated by the surgeon or operator to seize, hold and release pieces of the disc. The second tool may be formed similar to forceps or other tools having movable opposing jaws, or at least one movable opposing jaw. Particles may be viewed using a scope or a camera, or by injecting a contrast agent and visualizing or imaging the particles under fluoroscopy.

The second tool regains its S-shape as it exits the first sheath at an end of the sheath that is distal to the surgeon or other operator. As with other embodiments of the present invention, the combination of the S-shape with the manipulation of the first sheath within the disc allows portions of the S-shaped tool to be exposed as desired, so that all, or substantially all, portions of the disc may be accessed by the S-shaped tool.

Figure 47:
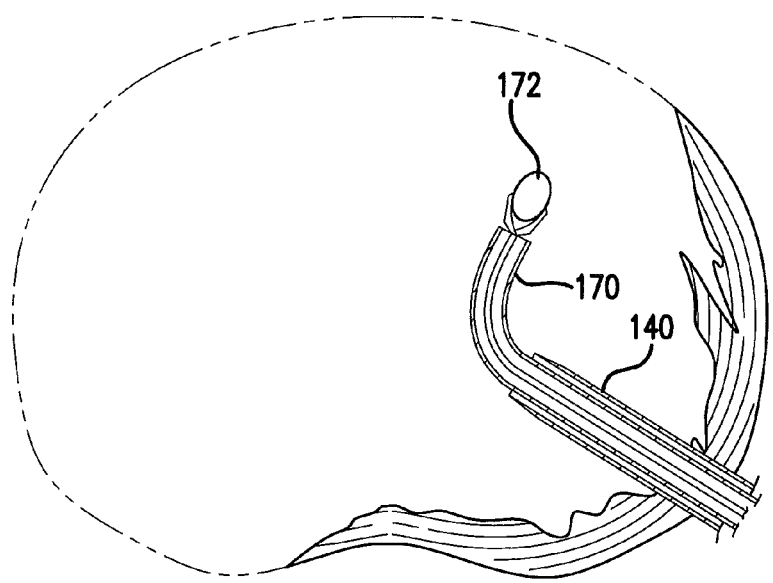
FIG. 47 demonstrates removing material from the disc by grasping material and withdrawing the material using a remotely actuated grasping tool.
Figure 48:
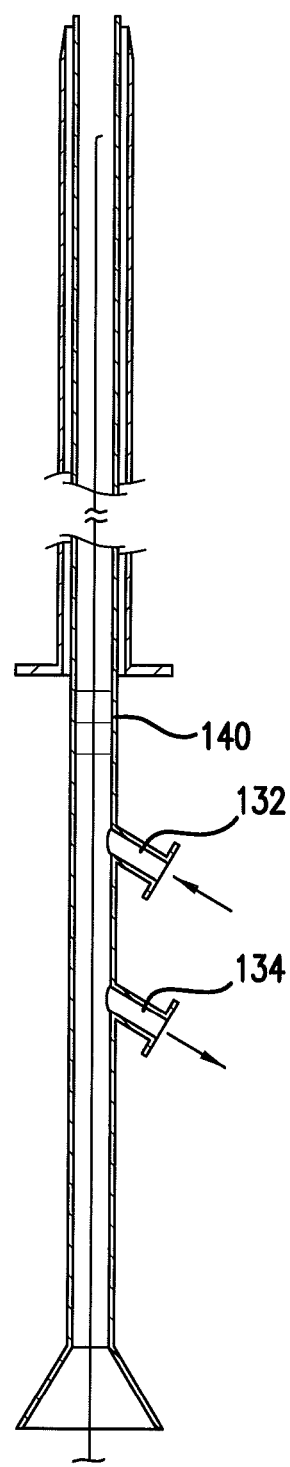
FIG. 48 is a sectioned view of an introducer having ports through which materials may be inserted into the disc, or from which materials may be removed, such as by vacuuming, or through which lavage may be provided.

After removal of larger particles or pieces of the disc, by the second S-shaped tool grasping such pieces or particles and successively withdrawing them through the first and/or second lumen. FIG. 47. Smaller pieces may be removed by lavage and suction. The sheath 140 may provide one or more ports 132, 134 for lavage and suction. FIG. 48. The ports may also be used to provide pressure for placement of the fusing agent under pressure through a lumen. The lumen may be present in an S-shaped tool.

After substantially all of the loose pieces of the disc are removed, a third S-shaped tool is introduced through the first sheath. The third S-shaped tool is preferred to have a scraper that scrapes and/or abrades the end-plate of the superior and inferior vertebral bodies. The third S-shaped tool 96 may be like the scraper 98 shown in FIG. 39. The process of scraping or abrading the end-plate of the superior and inferior vertebral bodies is intended to freshen the bone for purposes of fusion. The third S-shaped tool may be pre-positioned in a sheath for convenient insertion by the surgeon or operator into the first sheath, as described with the other S-shaped tools. As the third S-shaped tool exits the end of the first sheath, the third S-shaped tool may be manipulated relative to the first sheath and within the disc to reach all, or substantially all, portions of the vertebral body endplates.

The disc space has now been prepared for application of a fusing agent into the disc space. Known fusing agents may be applied to the disc. According to one embodiment, morselized bone is placed through a lumen and into the disc, such as through the lumen of the first sheath. Morphogenic protein may also be inserted through a lumen, such as the lumen of the first sheath. FIG. 3 shows a tool positioned at the end of the S-shaped tool 92 that is useful for placing the fusing agent. In one embodiment, the tool has opposing spoons 94 or scoops that form a clam shell device. The user manipulates the opposing spoons or scoops to grasp and release material or objects. The spoons or clam shell may be manipulated from an external position by the user through an actuator traversing the elongated portion of the tool and/or the sheath that extends to the interior of the disc.

An alternate method of placing a material such as morselized bone includes coating or packing the spacer or other physical object with the material, which may be a fusing agent and/or a medicament, prior to insertion of the spacer. Other means for injecting or advancing fusing agent are considered embodiments.

In some embodiments, it may also be desirable to place one or more spacers between vertebral bodies as described herein. The spacers may be positioned before or after the fusing agent is introduced into the disc space. The spacers may be positioned as shown in FIGS. 34 and 36.

Each embodiment of the tool may comprise an elongated tool having an S-shape, whether the tool is used as a conduit, a therapeutic tool, a tissue (or object) removal tool or a placement tool. The elongated tool in these forms comprises shape memory properties, so that the tool can be formed for transport through the guide or lumen of the introducer. The elongated tool regains its S-shape upon exiting the guide or lumen of the introducer. Similarly to the tool shown in FIGS. 5 through 15, an introducer and an elongated S-shaped tool can be manipulated independently of each other to advance and retract the introducer within the disc or vertebral body, and to expose as much of the S-shaped tool as is required relative to the introducer. The elongated S-shaped tool may thereby be positioned as desired within the disc or the vertebral body. The elongated S-shaped tool allows precise positioning of the tool, and therefore precise positioning of material. The elongated S-shaped tool also allows gross positioning of material where precision placement is not required.

The procedures and processes described herein may be, and are preferred to be, performed percutaneously. The procedures and processes may be performed using stab incision or small incision techniques, or techniques wherein an incision of about 3.0 centimeters or less is used to provide access for the introducer, the sheath and/or the tool.

What is claimed is:

1. A method of fusing mammalian vertebral bodies, comprising the steps of:
   a) advancing through an opening in a wall of a mammalian intervertebral disc a sheath comprising a lumen, wherein said lumen extends into the interior of the mammalian intervertebral disc;
   b) with said sheath in position in said opening of said mammalian intervertebral disc, engaging an elongated tool formed of a shape memory material and comprising a preformed S-shape with said lumen, and advancing said elongated tool along said lumen, wherein said preformed S-shape of said elongated tool is deformed by said lumen while said preformed S-shape engages said lumen;
   c) continuing to advance said elongated tool along said lumen until a portion of said elongated tool comprising said preformed S-shaped elongated tool exits said lumen into the interior of the mammalian intervertebral disc, whereupon the preformed S-shape of said elongated tool assumes said preformed S-shape as said elongated tool exits said lumen in the interior of the mammalian intervertebral disc;
   d) positioning said elongated tool as desired within the interior of the mammalian intervertebral disc, and minimizing contents of the intervertebral disc, wherein the elongated tool is selectively and progressively positioned as desired in the interior of the mammalian intervertebral disc by combining selective advancement and retraction of the elongated tool within the interior of the mammalian intervertebral disc with independent selective advancement and retraction of the sheath; and
   e) placing a fusing agent within said intervertebral disc.

2. A method of fusing mammalian vertebral bodies according to claim 1, wherein said elongated tool comprises a cutter.

3. A method of fusing mammalian vertebral bodies according to claim 1, wherein said elongated tool comprises a grinder.

4. A method of fusing mammalian vertebral bodies according to claim 1, further comprising the step of removing minimized contents of the intervertebral disc from the intervertebral disc.

5. A method of fusing mammalian vertebral bodies according to claim 1, further comprising the step of removing minimized contents of the intervertebral disc from the intervertebral disc using a second elongated tool formed of a shape memory material and comprising a preformed S-shape.

6. A method of fusing mammalian vertebral bodies according to claim 1, further comprising the step of removing minimized contents of the intervertebral disc from the intervertebral disc using a second elongated tool formed of a shape memory material and comprising a preformed S-shape by advancing said second elongated tool along said lumen until a portion of said elongated tool comprising said preformed S-shaped elongated tool exits said lumen into the interior of the mammalian intervertebral disc, whereupon the preformed S-shape of said elongated tool assumes said preformed S-shape as said elongated tool exits said lumen in the interior of the mammalian intervertebral disc, and positioning said elongated tool as desired within the interior of the mammalian intervertebral disc to contact said minimized contents for removal by said second elongated tool.

7. A method of fusing mammalian vertebral bodies according to claim 1, further comprising the step of removing minimized contents of the intervertebral disc from the intervertebral disc using suction.

8. A method of fusing mammalian vertebral bodies according to claim 1, further comprising the step of scraping an endplate of a vertebral body prior to placing the fusing agent.

9. A method of fusing mammalian vertebral bodies according to claim 1, wherein said elongated tool comprises a device for emitting radio frequency.

10. A method of fusing mammalian vertebral bodies according to claim 1, wherein said elongated tool comprises a device for emitting heat.

11. A method of fusing mammalian vertebral bodies according to claim 1, wherein said sheath comprises two lumens that longitudinally traverse a length of said sheath.

12. A method of fusing mammalian vertebral bodies according to claim 1, wherein said sheath comprises two lumens that longitudinally traverse a length of said sheath, and wherein said fusing agent is transported through at one of said two lumens of said sheath.

13. A method of fusing mammalian vertebral bodies according to claim 1, wherein said fusing agent is placed by a second S-shaped elongated tool.

14. A method of fusing mammalian vertebral bodies according to claim 1, wherein said fusing agent is placed by a second S-shaped elongated tool, and said second S-shaped elongated tool comprises forceps.

15. A method of fusing mammalian vertebral bodies according to claim 1, wherein said fusing agent is placed by a second S-shaped elongated tool, and said second S-shaped elongated tool comprises a lumen, and said fusing agent is transported through said lumen for placement in said intervertebral disc forceps.

16. A method of fusing mammalian vertebral bodies according to claim 1, wherein said elongated tool comprises means for removing tissue from the interior of the mammalian intervertebral disc.

17. A method of fusing mammalian vertebral bodies according to claim 1, wherein said sheath comprises a substantially straight lumen.

18. A method of fusing mammalian vertebral bodies according to claim 1, wherein said sheath comprises a substantially straight lumen and forms at least a portion of said elongated tool as straight as said elongated tool is transported through said lumen.

19. A method of fusing mammalian vertebral bodies according to claim 1, wherein said sheath comprises a side portal.

20. A method of fusing mammalian vertebral bodies according to claim 1, further comprising the step of positioning a spacer in the interior of the mammalian intervertebral disc.

21. A method of fusing mammalian vertebral bodies according to claim 1, wherein positioning of said elongated tool as desired within the interior of the mammalian intervertebral disc is performed by advancing and retracting said sheath through the opening in the wall of the mammalian intervertebral disc and into the interior of the mammalian intervertebral disc, and advancing and retracting said elongated tool relative to said sheath.

22. A method of fusing mammalian vertebral bodies according to claim 1, wherein the elongated tool is further selectively and progressively positioned as desired in the interior of the mammalian intervertebral disc by rotating the elongated tool relative to the sheath.

23. A method of fusing mammalian vertebral bodies according to claim 1, further comprising the step of positioning a spacer comprising a fusing agent in the interior of the mammalian intervertebral disc.

* * * * *